United States Patent
Nesvadba

Patent Number: 5,356,966
Date of Patent: Oct. 18, 1994

[54] 3-(CARBOXYMETHOXYPHENYL)BENZOFURAN-2-ONE STABILISERS

[75] Inventor: Peter Nesvadba, Marly, Switzerland

[73] Assignee: Ciba-Geigy Corporation, Ardsley, N.Y.

[21] Appl. No.: 64,193

[22] Filed: May 17, 1993

[30] Foreign Application Priority Data

May 22, 1992 [CH] Switzerland ............ 1653/92

[51] Int. Cl.$^5$ ............................................. C08K 5/15
[52] U.S. Cl. ............................ 524/111; 514/126; 514/128
[58] Field of Search ........................................... 514/111

[56] References Cited

U.S. PATENT DOCUMENTS

| | | | |
|---|---|---|---|
| 4,325,863 | 4/1982 | Hinsken et al. | 524/94 |
| 4,338,244 | 7/1982 | Hinsken et al. | 524/109 |
| 5,308,899 | 5/1994 | Michaelis | 524/109 |

FOREIGN PATENT DOCUMENTS

| | | |
|---|---|---|
| 0146269 | 6/1985 | European Pat. Off. . |
| 0294029 | 12/1988 | European Pat. Off. . |
| 0415887 | 3/1991 | European Pat. Off. . |
| 543778 | 5/1993 | European Pat. Off. . |
| 4202276 | 8/1992 | Fed. Rep. of Germany . |
| 2205324 | 12/1988 | United Kingdom . |
| 2034308 | 6/1990 | United Kingdom . |

OTHER PUBLICATIONS

W. Bradley, et al., J. Chem. Soc. 1956, 1622.
Organikum 1986 pp. 194–200.
Houben–Weyl Methoden der organischen Chemie, vol. 6/1C, 1030.
Organikum 1986, pp. 402–410.

Primary Examiner—Kriellion S. Morgan
Attorney, Agent, or Firm—Luther A. R. Hall

[57] ABSTRACT

Compounds of the formula (1),

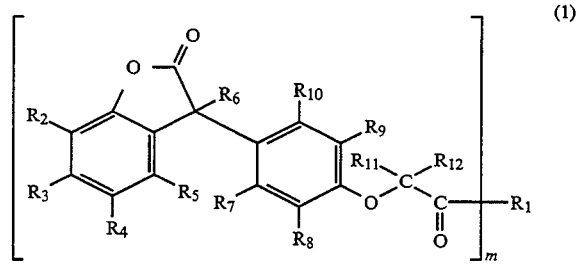

in which $R_2$, $R_3$, $R_4$ and $R_5$, independently of one another, are hydrogen, $C_1$–$C_{25}$alkyl, $C_7$–$C_9$phenylalkyl, unsubstituted or $C_1$–$C_4$alkyl-substituted phenyl, unsubstituted or $C_1$–$C_4$alkyl-substituted $C_5$–$C_8$cycloalkyl; $C_1$–$C_{18}$alkoxy, hydroxyl, $C_1$–$C_{25}$alkanoyloxy, $C_3$–$C_{25}$alkenoyloxy, $C_3$–$C_{25}$alkanoyloxy which is interrupted by oxygen, sulfur or >N—$R_{13}$; $C_6$–$C_9$cycloalkylcarbonyloxy, benzoyloxy or $C_1$–$C_{12}$alkyl-substituted benzoyloxy, in which $R_{13}$ is hydrogen or $C_1$–$C_{18}$alkyl, or furthermore the radicals $R_2$ and $R_3$ or the radicals $R_4$ and $R_5$ together with the carbon atoms to which they are bonded form a phenyl ring, $R_4$ is additionally $(CH_2)_n$—$COR_{14}$, in which n is 0, 1 or 2, $R_{14}$ is hydroxyl,

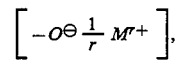

$C_1$–$C_{18}$alkoxy or

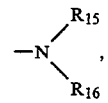

$R_{15}$ and $R_{16}$, independently of one another, are hydrogen or $C_1$–$C_{18}$alkyl, M is an r-valent metal cation and r is 1, 2 or 3, $R_7$, $R_8$, $R_9$ and $R_{10}$, independently of one another, are hydrogen, $C_1$–$C_4$alkyl or $C_1$–$C_4$alkoxy, with the proviso that at least one of the radicals $R_7$, $R_8$, $R_9$ and $R_{10}$ is hydrogen, $R_{11}$ and $R_{12}$, independently of (Abstract continued on next page.)

one another, are hydrogen, $C_1$–$C_4$alkyl or phenyl, and, in the case where $R_3$, $R_5$, $R_6$, $R_7$ and $R_{10}$ are hydrogen, $R_4$ is additionally a radical of the formula (2),

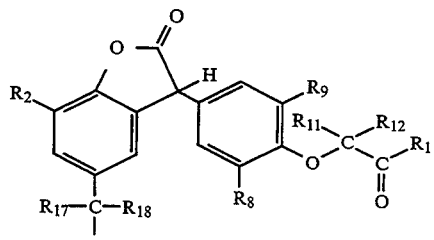
(2)

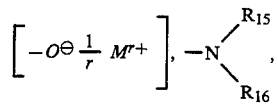

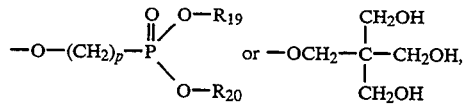

$R_{16}$, r and M are as defined above, $R_{19}$ and $R_{20}$, independently of one another, are $C_1$–$C_4$alkyl, p is 1 or 2, and $R_6$ is hydrogen or a radical of the formula (3),

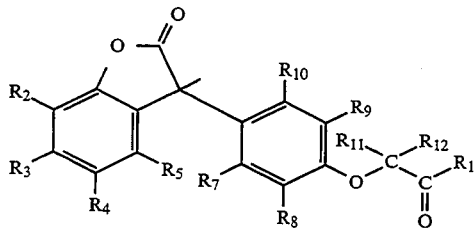
(3)

in which $R_2$, $R_8$, $R_9$, $R_{11}$ and $R_{12}$ are as defined above and $R_1$ is as defined below for m=1 and $R_{17}$ and $R_{18}$, independently of one another, are hydrogen, $C_1$–$C_{12}$alkyl or phenyl, or $R_{17}$ and $R_{18}$ together with the carbon atom to which they are bonded form a $C_5$–$C_7$cycloalkylidene ring which is unsubstituted or substituted by 1 to 3 $C_1$–$C_4$alkyl, m is an integer from the range of 1 to 6, and, in the case where m is 1, $R_1$ is hydroxyl, $C_1$–$C_{30}$alkoxy, $C_3$–$C_{30}$alkoxy which is interrupted by oxygen, sulfur or >N—$R_{13}$; $C_7$–$C_9$phenylalkoxy, $C_5$–$C_{12}$cycloalkoxy, $C_2$–$C_{18}$alkenyloxy, unsubstituted or $C_1$–$C_{12}$alkyl-substituted phenoxy, in which $R_1$, $R_2$, $R_3$, $R_4$, $R_5$, $R_7$, $R_8$, $R_9$, $R_{10}$, $R_{11}$ and $R_{12}$ are as defined above, are described as stabilizers for organic materials against thermal, oxidative or light-induced degradation.

12 Claims, No Drawings

3-(CARBOXYMETHOXYPHENYL)BENZOFURAN-2-ONE STABILISERS

The present invention relates to compositions comprising an organic material, preferably a polymer, and 3-(carboxymethoxyphenyl)benzofuran-2-ones as stabilisers, to the use of same for the stabilisation of organic materials against oxidative, thermal or light-induced degradation and to novel 3-(carboxymethoxyphenyl)-benzofuran-2-ones.

Individual 3-(carboxymethoxyphenyl)benzofuran-2-ones have been described, for example, in GB-A-2 205 324 and EP-A-294 029.

The use of individual benzofuran-2-ones as stabilisers for organic polymers is disclosed, for example, in U.S. Pat. Nos. 4,325,863; 4,338,244 and EP-A-415 887.

It has now been found that a selected group of such benzofuran-2-ones is particularly suitable as stabilisers for organic materials which are sensitive to oxidative, thermal or light-induced degradation.

Accordingly, the present invention provides compositions comprising a) an organic material subject to oxidative, thermal or light-induced degradation and b) at least one compound of the formula (1),

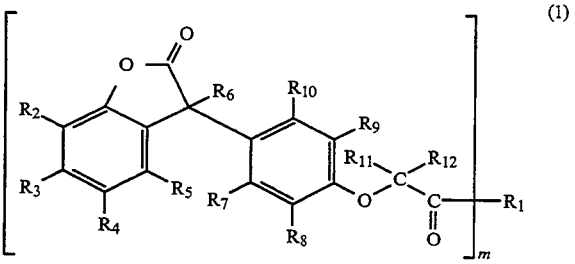

(1)

in which $R_2$, $R_3$, $R_4$ and $R_5$, independently of one another, are hydrogen, $C_1$–$C_{25}$alkyl, $C_7$–$C_9$phenylalkyl, unsubstituted or $C_1$–$C_4$alkyl-substituted phenyl, unsubstituted or $C_1$–$C_4$alkyl-substituted $C_5$–$C_8$cycloalkyl; $C_1$–$C_{18}$alkoxy, hydroxyl, $C_1$–$C_{25}$alkanoyloxy, $C_3$–$C_{25}$alkenoyloxy, $C_3$–$C_{25}$alkanoyloxy which is interrupted by oxygen, sulfur or >N—$R_{13}$; $C_6$–$C_9$cycloalkylcarbonyloxy, benzoyloxy or $C_1$–$C_{12}$alkyl-substituted benzoyloxy, in which $R_{13}$ is hydrogen or $C_1$–$C_8$alkyl, or furthermore the radicals $R_2$ and $R_3$ or the radicals $R_4$ and $R_5$ together with the carbon atoms to which they are bonded form a phenyl ring, $R_4$ is additionally $(CH_2)_n$—$COR_{14}$, in which n is 0, 1 or 2, $R_{14}$ is hydroxyl,

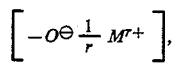

$C_1$–$C_{18}$alkoxy or

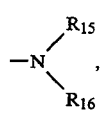

$R_{15}$ and $R_{16}$, independently of one another, are hydrogen or $C_1$–$C_{18}$alkyl, M is an r-valent metal cation and r is 1, 2 or 3, $R_7$, $R_8$, $R_9$ and $R_{10}$, independently of one another, are hydrogen, $C_1$–$C_4$alkyl or $C_1$–$C_4$alkoxy, with the proviso that at least one of the radicals $R_7$, $R_8$, $R_9$ and $R_{10}$ is hydrogen, $R_{11}$ and $R_{12}$, independently of one another, are hydrogen, $C_1$–$C_4$alkyl or phenyl, and, in the case where $R_3$, $R_5$, $R_6$, $R_7$ and $R_{10}$ are hydrogen, $R_4$ is additionally a radical of the formula (2),

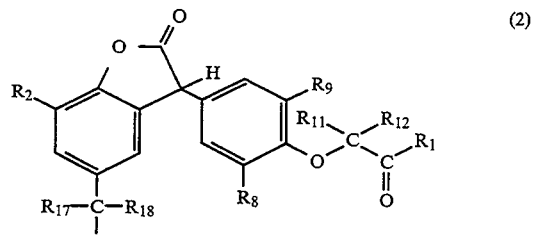

(2)

in which $R_2$, $R_8$, $R_9$, $R_{11}$ and $R_{12}$ are as defined above and $R_1$ is as defined below for m=1 and $R_{17}$ and $R_{18}$, independently of one another, are hydrogen, $C_1$–$C_{12}$alkyl or phenyl, or $R_{17}$ and $R_{18}$ together with the carbon atom to which they are bonded form a $C_5$–$C_7$cycloalkylidene ring which is unsubstituted or substituted by 1 to 3 $C_1$–$C_4$alkyl, m is an integer from the range of 1 to 6, and, in the case where m is 1, $R_1$ is hydroxyl, $C_1$–$C_3$₀alkoxy, $C_3$–$C_{30}$alkoxy which is interrupted by oxygen, sulfur or >N—$R_{13}$; $C_7$–$C_9$phenylalkoxy, $C_5$–$C_{12}$cycloalkoxy, $C_2$–$C_{18}$alkenyloxy, unsubstituted or $C_1$–$C_{12}$alkyl-substituted phenoxy,

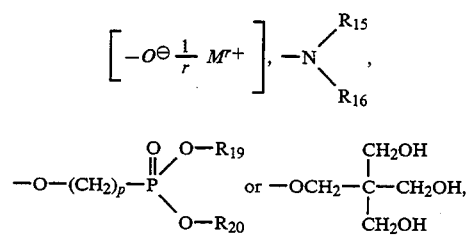

$R_{16}$, r and M are as defined above, $R_{19}$ and $R_{20}$, independently of one another, are $C_1$–$C_4$alkyl, p is 1 or 2, and $R_6$ is hydrogen or a radical of the formula (3),

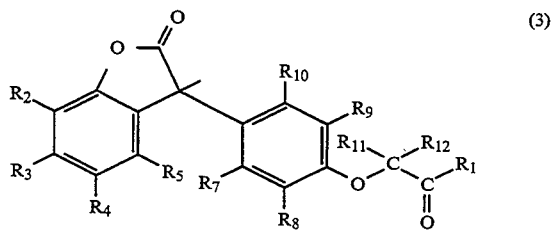

(3)

in which $R_1$, $R_2$, $R_3$, $R_4$, $R_5$, $R_7$, $R_8$, $R_9$, $R_{10}$, $R_{11}$ and $R_{12}$ are as defined above; or, in the case where m is 2, $R_1$ is $C_2$–$C_{12}$alkanedioxy, $C_3$–$C_{25}$alkanedioxy which is interrupted by oxygen, sulfur or >N—$R_{13}$,

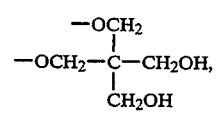

—OCH$_2$—CH=CH—CH$_2$O— or —OCH$_2$—C≡C—CH$_2$O—, in which $R_{13}$ is as defined above; or, in the case where m is 3, $R_1$ is $C_3$–$C_{10}$alkanetrioxy,

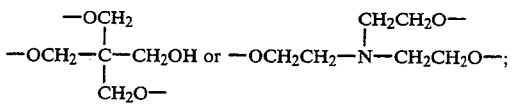

or, in the case where m is 4, $R_1$ is $C_4$-$C_{10}$alkanetetraoxy,

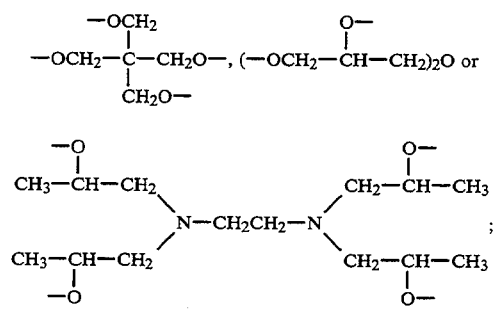

or, in the case where m is 5, $R_1$ is $C_5$-$C_{10}$alkanepentaoxy; or in the case where m is 6, $R_1$ is $C_6$-$C_{10}$alkanehexaoxy or

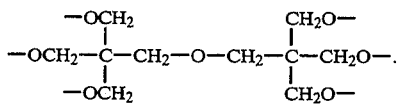

Alkyl of up to 25 carbon atoms is a branched or unbranched radical, for example methyl, ethyl, propyl, isopropyl, n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl, dodecyl, 1,1,3,3,5,5-hexamethylhexyl, tridecyl, tetradecyl, pentadecyl, hexadecyl, heptadecyl, octadecyl, eicosyl or docosyl. An example of one of the preferred meanings of $R_2$ and $R_4$ is $C_1$-$C_{18}$alkyl. A particularly preferred meaning of $R_4$ is $C_1$-$C_4$alkyl.

Examples of $C_7$-$C_9$phenylalkyl are benzyl, α-methylbenzyl, α,α-dimethylbenzyl or 2-phenylethyl. Benzyl is preferred.

Examples of $C_1$-$C_4$alkyl-substituted phenyl which, preferably, contains 1 to 3, in particular 1 or 2, alkyl groups, are o-, m- or p-methylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2-methyl-6-ethylphenyl, 4-tert-butylphenyl, 2-ethylphenyl or 2,6-diethylphenyl.

Examples of unsubstituted or $C_1$-$C_4$alkyl-substituted $C_5$-$C_8$cycloalkyl are cyclopentyl, methylcyclopentyl, dimethylcyclopentyl, cyclohexyl, methylcyclohexyl, dimethylcyclohexyl, trimethylcyclohexyl, tert-butylcyclohexyl, cycloheptyl or cyclooctyl. Cyclohexyl and tert-butylcyclohexyl are preferred.

Alkoxy of up to 30 carbon atoms is a branched or unbranched radical, for example methoxy, ethoxy, propoxy, isopropoxy, n-butoxy, isobutoxy, pentoxy, isopentoxy, hexoxy, heptoxy, octoxy, decyloxy, tetradecyloxy, hexadecyloxy or octadecyloxy.

Alkanoyloxy of up to 25 carbon atoms is a branched or unbranched radical, for example formyloxy, acetyloxy, propionyloxy, butanoyloxy, pentanoyloxy, hexanoyloxy, heptanoyloxy, octanoyloxy, nonanoyloxy, decanoyloxy, undecanoyloxy, dodecanoyloxy, tridecanoyloxy, tetradecanoyloxy, pentadecanoyloxy, hexadecanoyloxy, heptadecanoyloxy, octadecanoyloxy, eicosanoyloxy or docosanoyloxy.

Alkenoyloxy of 3 to 25 carbon atoms is a branched or unbranched radical, for example propenoyloxy, 2-butenoyloxy, 3-butenoyloxy, isobutenoyloxy, n-2,4-pentadienoyloxy, 3-methyl-2-butenoyloxy, n-2-octenoyloxy, n-2-dodecenoyloxy, iso-dodecenoyloxy, oleoyloxy, n-2-octadecenoyloxy or n-4-octadecenoyloxy.

Examples of $C_3$-$C_{25}$alkanoyloxy which is interrupted by oxygen, sulfur or $>N-R_{16}$ are $CH_3-O-CH_2COO-$, $CH_3-S-CH_2COO-$, $CH_3-NH-CH_2COO-$, $CH_3-N(CH_3)-CH_2COO-$, $CH_3-O-CH_2CH_2-O-CH_2COO-$, $CH_3-(O-CH_2CH_2-)_2O-CH_2COO-$, $CH_3-(O-CH_2CH_2-)_3O-CH_2COO-$ or $CH_3-(O-CH_2CH_2-)_4O-CH_2COO-$.

Examples of $C_6$-$C_9$cycloalkylcarbonyloxy are cyclopentylcarbonyloxy, cyclohexylcarbonyloxy, cycloheptylcarbonyloxy or cyclooctylcarbonyloxy. Cyclohexylcarbonyloxy is preferred.

Examples of $C_1$-$C_{12}$alkyl-substituted benzoyloxy are o-, m- or p-methylbenzoyloxy, 2,3-dimethylbenzoyloxy, 2,4-dimethylbenzoyloxy, 2,5-dimethylbenzoyloxy, 2,6-dimethylbenzoyloxy, 3,4-dimethylbenzoyloxy, 3,5-dimethylbenzoyloxy, 2-methyl-6-ethylbenzoyloxy, 4-tert-butylbenzoyloxy, 2-ethylbenzoyloxy, 2,4,6-trimethylbenzoyloxy, 2,6-dimethyl-4-tert-butylbenzoyloxy or 3,5-di-tert-butylbenzoyloxy.

Examples of a $C_5$-$C_7$cycloalkylidene ring which is unsubstituted or substituted by 1 to 3 $C_1$-$C_4$alkyl are cyclopentylidene, methylcyclopentylidene, dimethylcyclopentylidene, cyclohexylidene, methylcyclohexylidene, dimethylcyclohexylidene, trimethylcyclohexylidene, tert-butylcyclohexylidine or cycloheptylidene. Cyclohexylidene and tert-butylcyclohexylidene are preferred.

Examples of $C_3$-$C_{30}$alkoxy which is interrupted by oxygen, sulfur or $>N-R_{16}$ are $CH_3-O-CH_2CH_2O-$, $CH_3-S-CH_2CH_2O-$, $CH_3-NH-CH_2CH_2O-$, $CH_3-N(CH_3)-CH_2CH_2O-$, $CH_3-O-CH_2CH_2-O-CH_2CH_2O-$, $CH_3-(O-CH_2CH_2-)_2O-CH_2CH_2O-$, $CH_3-(O-CH_2CH_2-)_3O-CH_2CH_2O-$ or $CH_3-(O-CH_2CH_2-)_4O-CH_2CH_2O-$.

Examples of $C_7$-$C_9$phenylalkoxy are benzyloxy, α-methylbenzyloxy, α,α-dimethylbenzyloxy or 2-phenylethyloxy. Benzyloy is preferred.

Examples of cycloalkoxy of 5 to 12 C atoms are cyclopentoxy, cyclohexoxy, cycloheptoxy, cyclooctoxy, cyclodecyloxy or cyclododecyloxy. $C_5$-$C_8$Cycloalkoxy is preferred.

Alkenyloxy of 2 to 18 carbon atoms is a branched or unbranched radical, for example vinyloxy, propenyloxy, 2-butenyloxy, 3-butenyloxy, isobutenyloxy, n-2,4-pentadienyloxy, 3-methyl-2-butenyloxy, n-2-octenyloxy, n-2-dodecenyloxy, iso-dodecenyloxy, oleyloxy, n-2-octadecenyloxy or n-4-octadecenyloxy.

Examples of $C_1$-$C_{12}$alkyl-substituted phenoxy which, preferably, contains 1 to 3, in particular 1 or 2, alkyl groups are o-, m- or p-methylphenoxy, 2,3-dimethylphenoxy, 2,4-dimethylphenoxy, 2,5-dimethylphenoxy, 2,6-dimethylphenoxy, 3,4-dimethylphenoxy, 3,5-dimethylphenoxy, 2-methyl-6-ethylphenoxy, 4-tert-butylphenoxy, 2-ethylphenoxy or 2,6-diethylphenoxy.

Alkanedioxy of 2 to 12 C atoms is a branched or unbranched radical, for example —OCH$_2$CH$_2$O—, —OCH$_2$CH$_2$CH$_2$O—, —OCH$_2$CH$_2$CH$_2$CH$_2$O—, —OCH$_2$CH$_2$CH$_2$CH$_2$CH$_2$O— or —OCH(CH$_3$)CH$_2$CH(CH$_3$)O—.

Examples of C$_3$-C$_{25}$alkanedioxy which is interrupted by oxygen, sulfur or >N—R$_{16}$ are —OCH$_2$CH$_2$—S—CH$_2$CH$_2$O—, —OCH$_2$CH$_2$—NH—CH$_2$CH$_2$O—, —OCH$_2$CH$_2$—N(CH$_3$)—CH$_2$CH$_2$O—, —OCH$_2$CH$_2$OCH$_2$CH$_2$O—, —(O—CH$_2$CH$_2$—)$_2$O—CH$_2$CH$_2$O—, —(O—CH$_2$CH$_2$—)$_3$O—CH$_2$CH$_2$O— or —(O—CH$_2$CH$_2$—)$_4$O—CH$_2$CH$_2$O—.

Examples of alkanetrioxy of 3 to 10 C atoms are

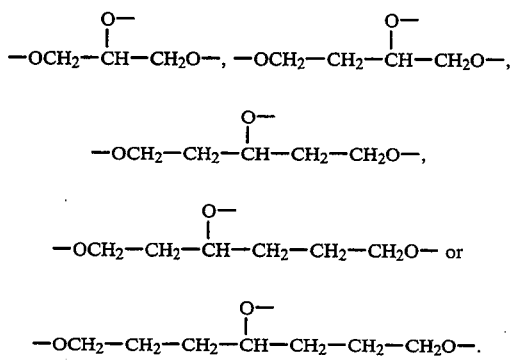

Examples of alkanetetraoxy of 4 to 10 C atoms are

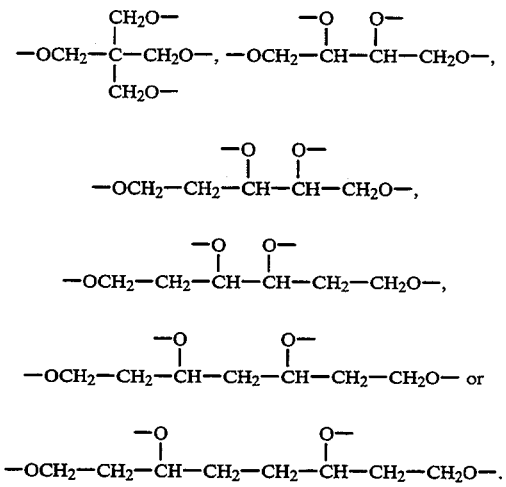

Examples of alkanepentaoxy of 5 to 10 C atoms are

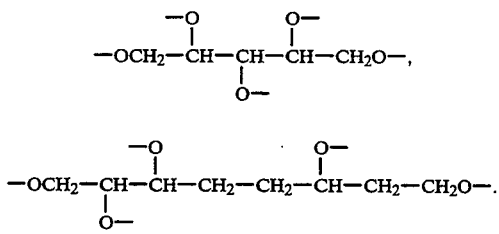

Examples of alkanehexaoxy of 6 to 10 C atoms are

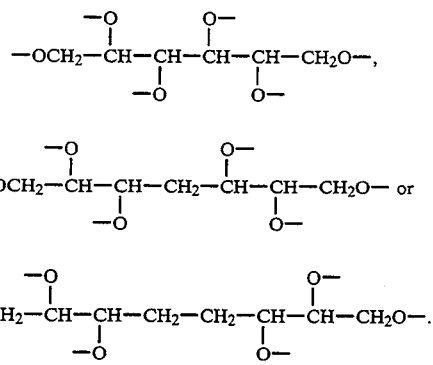

A mono-, di- or trivalent metal cation is preferably an alkali metal cation, alkaline earth metal cation or aluminium cation, for example Na$^+$, K$^+$, Mg$^{++}$, Ca$^{++}$ Al$^{+++}$.

Of interest are compositions containing compounds of the formula (1) in which R$_2$, R$_3$, R$_4$ and R$_5$, independently of one another, are hydrogen C$_1$-C$_{18}$alkyl, benzyl, phenyl, C$_5$-C$_8$cycloalkyl, C$_1$-C$_8$alkoxy, hydroxyl, C$_1$-C$_{18}$alkanoyloxy, C$_3$-C$_{18}$alkenoyloxy or benzoyloxy, R$_4$ is additionally —(CH$_2$)$_n$—COR$_{14}$, m is 1 to 4, and in the case where m is 1, R$_1$ is hydroxyl, C$_1$-C$_{18}$alkoxy, C$_3$-C$_{18}$alkoxy which is interrupted by oxygen, sulfur or >N—R$_{13}$; benzyloxy, C$_5$-C$_8$cycloalkoxy, unsubstituted or C$_1$-C$_8$alkyl-substituted phenoxy,

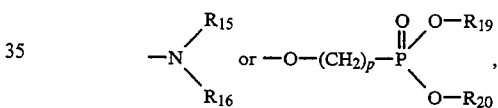

in which R$_{13}$, R$_{15}$, R$_{16}$, p, R$_{19}$ and R$_{20}$ are as defined above; or, in the case where m is 2, R$_1$ is C$_2$-C$_{12}$alkanedioxy or C$_3$-C$_{25}$alkanedioxy which is interrupted by oxygen; or, in the case where m is 3, R$_1$ is C$_3$-C$_{10}$alkanetrioxy; or, in the case where m is 4, R$_1$ is

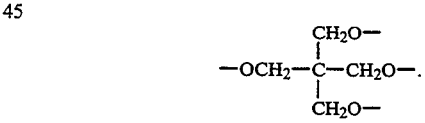

Preference is given to compositions in which in formula (1) at least two of the radicals R$_2$, R$_3$, R$_4$ and R$_5$ are hydrogen.

Preference is also given to compositions in which in formula (1) R$_3$ and R$_5$ are hydrogen.

Preference is also given to compositions in which in formula (1) m is 1.

Preference is also given to compositions in which in formula (1) R$_3$, R$_5$, R$_7$ and R$_{10}$, independently of one another, are hydrogen or C$_1$-C$_4$alkyl, R$_2$ is hydrogen or C$_1$-C$_{18}$alkyl, R$_4$ is hydrogen, C$_1$-C$_{12}$alkyl, C$_1$-C$_8$alkoxy or —(CH$_2$)$_n$—COR$_{14}$, in which n is 0, 1 or 2, R$_{14}$ is hydroxyl or C$_1$-C$_{12}$alkoxy, R$_{11}$ and R$_{12}$, independently of one another, are hydrogen or C$_1$-C$_4$alkyl, m is 1 and R$_1$ is hydroxyl, C$_1$-C$_{18}$alkoxy, C$_3$-C$_{18}$alkoxy which is interrupted by oxygen, unsubstituted or C$_1$-C$_8$alkyl-substituted phenoxy,

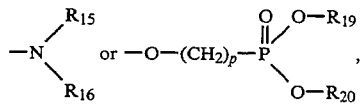

in which $R_{15}$ and $R_{16}$, independently of one another, are hydrogen or $C_1$-$C_{12}$alkyl.

Particular preference is given to compositions in which in formula (1) m is 1, $R_1$ is hydroxyl, $C_1$-$C_{18}$alkoxy, $C_3$-$C_{18}$alkoxy which is interrupted by oxygen, unsubstituted or $C_1$-$C_8$alkyl-substituted phenoxy,

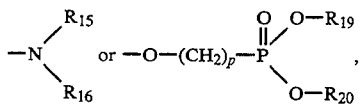

in which $R_{15}$ and $R_{16}$, independently of one another, are hydrogen or $C_1$-$C_{12}$alkyl, $R_2$ is hydrogen, $C_1$-$C_{18}$alkyl or cyclohexyl, $R_3$, $R_5$, $R_7$ and $R_{10}$ are hydrogen, or the radicals $R_2$ and $R_3$ together with the carbon atoms to which they are bonded form a phenyl ring, $R_4$ is hydrogen, $C_1$-$C_6$alkyl, cyclohexyl, $C_1$-$C_4$alkoxy or —(CH$_2$)$_2$—COR$_{14}$, in which $R_{14}$ is $C_1$-$C_4$alkyl, $R_8$, $R_9$, $R_{11}$ and $R_{12}$, independently of one another, are hydrogen or $C_1$-$C_4$alkyl, and, in the case where $R_6$ is hydrogen, $R_4$ is additionally a radical of the formula (2),

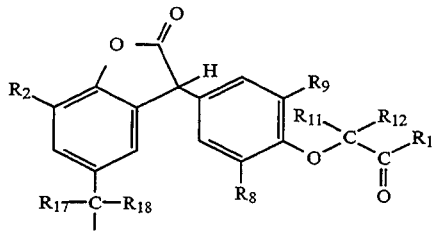

in which $R_1$, $R_2$, $R_8$, $R_9$, $R_{11}$ and $R_{12}$ are as defined above, $R_{17}$ and $R_{18}$, independently of one another, are hydrogen or $C_1$-$C_4$alkyl, or $R_{17}$ and $R_{18}$ together with the carbon atom to which they are bonded form a $C_5$-$C_7$cycloalkylidene ring, $R_6$ is hydrogen or a radical of the formula (3),

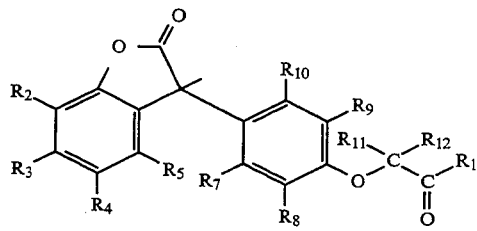

in which $R_1$, $R_2$, $R_3$, $R_4$, $R_5$, $R_7$, $R_8$, $R_9$, $R_{10}$, $R_{11}$ and $R_{12}$ are as defined above.

Specific preference is given to compositions in which in formula (1) m is 1, $R_1$ is hydroxyl, $C_1$-$C_{18}$alkoxy, unsubstituted or $C_1$-$C_4$alkyl-substituted phenoxy;

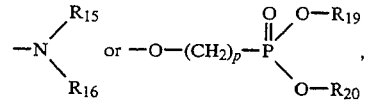

in which $R_{15}$ and $R_{16}$, independently of one another, are hydrogen or $C_1$-$C_4$alkyl, p is 1 or 2, and $R_{19}$ and $R_{20}$, are $C_1$-$C_4$alkyl, $R_2$ is hydrogen or $C_1$-$C_{18}$alkyl, $R_3$, $R_5$, $R_7$, $R_{10}$, $R_{11}$ and $R_{12}$ are hydrogen, $R_4$ is hydrogen or $C_1$-$C_4$alkyl, and, in the case where $R_6$ is hydrogen, $R_4$ is additionally a radical or the formula (2),

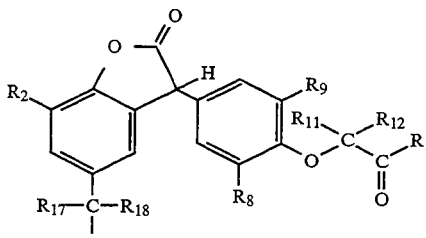

$R_{17}$ and $R_{18}$ together with the carbon atom to which they are bonded form a cyclohexylidene ring, $R_8$ and $R_9$, independently of one another, are hydrogen or $C_1$-$C_4$alkyl, $R_6$ is hydrogen or a radical of the formula (3),

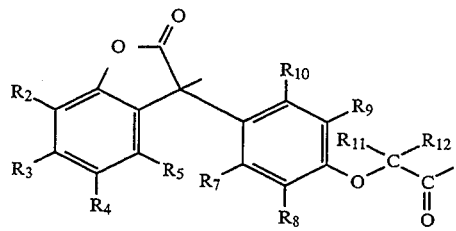

in which $R_1$, $R_2$, $R_3$, $R_4$, $R_5$, $R_7$, $R_8$, $R_9$, $R_{10}$, $R_{11}$ and $R_{12}$ are as defined above.

The compounds according to the invention of the formula (1) are suitable for the stabilisation of organic materials against thermal, oxidative or light-induced degradation.

Examples of such materials are:

1. Polymers of monoolefins and diolefins, for example polypropylene, polyisobutylene, polybut-1-ene, poly-4-methylpent-1-ene, polyisoprene or polybutadiene, as well as polymers of cycloolefins, for instance of cyclopentene or norbornene, polyethylene (which optionally can be crosslinked), for example high density polyethylene (HDPE), low density polyethylene (LDPE), linear low density polyethylene (LLDPE), branched low density polyethylene (BLDPE).

Polyolefins, i.e. the polymers of monoolefins exemplified in the preceding paragraph, preferably polyethylene and polypropylene, can be prepared by different, and especially by the following, methods:

a) radical polymerisation (normally under high pressure and at elevated temperature).

b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either π- or σ-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethy-lidenenorbornene; and mixtures of such copolymers with one mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

4. Hydrocarbon resins (for example C5–C9) including hydrogenated modifications thereof (e.g. tackifiers) and mixtures of polyalkylenes and starch.

5. Polystyrene, poly(p-methylstyrene), poly(α-methylstyrene).

6. Copolymers of styrene or α-methylstyrene with dienes or acrylic derivatives, for example styrene/butadiene, styrene/acrylonitrile, styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylene/butylene/styrene or styrene/ethylene/propylene/styrene.

7. Graft copolymers of styrene or α-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from α, β-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer; polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

17. Polyureas, polyimides, polyamide-imides and polybenzimidazoles.

18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate and polyhydroxybenzoates, as well as block copolyether esters derived from hydroxyl-terminated polyethers; and also polyesters modified with polycarbonates or MBS.

19. Polycarbonates and polyester carbonates.

20. Polysulfones, polyether sulfones and polyether ketones.

21. Crosslinked polymers derived from aldehydes on the one hand and phenols, ureas and melamines on the other hand, such as phenol/formaldehyde resins, urea/formaldehyde resins and melamine/formaldehyde resins.

22. Drying and non-drying alkyd resins.

23. Unsaturated polyester resins derived from copolyesters of saturated and unsaturated dicarboxylic acids with polyhydric alcohols and vinyl compounds as crosslinking agents, and also halogen-containing modifications thereof of low flammability.

24. Crosslinkable acrylic resins derived from substituted acrylates, for example epoxy acrylates, urethane acrylates or polyester acrylates.

25. Alkyd resins, polyester resins and acrylate resins crosslinked with melamine resins, urea resins, polyisocyanates or epoxy resins.

26. Crosslinked epoxy resins derived from polyepoxides, for example from bisglycidyl ethers or from cycloaliphatic diepoxides.

27. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.

28. Blends of the aforementioned polymers (polyblends), for example PP/EPDM, Polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO.

29. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, typically those used as spinning compositions, as well as aqueous emulsions of such materials.

30. Aqueous emulsions of natural or synthetic rubber, e.g. natural latex or latices of carboxylated styrene/butadiene copolymers.

Preferred organic materials are polymers, for example synthetic polymers, in particular thermoplastic polymers. Polyolefins, for example polypropylene or polyethylene are particularly preferred.

The effect of the compounds according to the invention against thermal and oxidative degradation, in particular under thermal stress, such as occurs during the processing of thermoplastics, may be mentioned in particular. Therefore, the compounds according to the invention are highly suitable for use as process stabilisers.

Preferably, the compounds of the formula (1) are added to the material to be stabilised in amounts of 0.0005 to 5%, in particular 0.001 to 2%, for example 0.01 to 2%, relative to the weight of the organic material to be stabilised.

The compositions according to the invention can contain, in addition to the compounds of the formula (1) further co-stabilisers, for example the ones listed below:

1. Antioxidants 1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, 2,6-di-nonyl-4-methylphenol, 2,4-dimethyl-6-(1'-methylundec-1'-yl)phenol, 2,4-dimethyl-6-(1'-methylheptadec-1'-yl)phenol, 2,4-dimethyl-6-(1'-methyltridec-1'-yl)phenol and mixtures thereof.

1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-do-decylthiomethyl-4-nonylphenol.

1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis-(3,5-di-tert-butyl-4-hydroxyphenyl) adipate.

1.4. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis(3,6-di-sec-amylphenol), 4,4'-bis-(2,6-dimethyl-4-hydroxyphenyl) disulfide.

1.5. Alkylidenebisphenols, for example 2,2'-methylenebis(6-tert-butyl-a-methylphenol), 2,2'-methylenebis(6-tert-butyl-4-ethylphenol), 2,2'-methylenebis[4-methyl-6-(α-methylcyclohexyl)-phenol],2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis([6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2- methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmercaptobutane, ethylene glycol bis[3,3-bis(3'-tert-butyl-4'-hydroxyphenyl)butyrate], bis(3-tert-butyl-4-hydroxy-5-methyl-phenyl)dicyclopentadiene, bis[2-(3'-tert-butyl-2'-hydroxy-5'-methylbenzyl)-6-tert-butyl-4-methylphenyl]terephthalate, 1,1-bis-(3,5-dimethyl-2-hydroxyphenyl)butane, 2,2-bis-(3,5-di-tert-butyl-4-hydroxyphenyl)propane, 2,2-bis-(5-tert-butyl-4-hydroxy2-methylphenyl)-4-n-dodecylmercaptobutane, 1,1,5,5-tetra-(5-tert-butyl-4-hydroxy2-methylphenyl)pentane.

1.6. O-, N- and S-benzyl compounds, for example 3,5,3',5'-tetra-tert-butyl-4,4'-dihydroxydibenzyl ether, octadecyl-4-hydroxy-3,5-dimethylbenzylmercaptoacetate, tris-(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxybenzyl)sulfide, isooctyl-3,5di-tert-butyl-4hydroxybenzylmercaptoacetate.

1.7. Hydroxybenzylated malonates, for example dioctadecyl-2,2-bis-(3,5-di-tert-butyl-2-hydroxybenzyl)-malonate, di-octadecyl-2-(3-tert-butyl-4-hydroxy-5-methylbenzyl)-malonate, di-dodecylmercaptoethyl-2,2-bis-(3,5-di-tert-butyl-4-hydroxybenzyl)malonate, bis-[4-(1,1,3,3-tetramethylbutyl)phenyl]-2,2-bis(3,5-di-tert-butyl-4-hydroxybenzyl)malonate.

1.8. Aromatic hydroxybenzyl compounds, for example 1,3,5-tris-(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl )phenol.

1.9. Triazine Compounds, for example 2,4-bis(octylmercapto)-6-(3,5-di-tert-butyl-4-hydroxyanilino)-1,3,5-triazine, 2-octylmercapto-4,6-bis(3,5-di-tert-butyl-4-hydroxyanilino)- 1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris(3,5-di-tert-butyl-4-hydroxybenzyl)isocyanurate, 1,3,5-tris(4-tert-butyl-3-hydroxy-2,6-dimethylbenzyl)isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl)isocyanurate.

1.10. Benzylphosphonates, for example dimethyl-2,5-di-tert-butyl-4-hydroxybenzylphosphonate, diethyl-3,5-di-tert-butyl-4-hydroxybenzylphosphonate, dioctadecyl3,5-di-tert-butyl-4-hydroxybenzylphosphonate, dioctadecyl-5-tert-butyl-4-hydroxy3-methylbenzylphosphonate, the calcium salt of the monoethyl ester of 3,5-di-tert-butyl-4-hydroxybenzylphosphonic acid.

1.11. Acylaminophenols, for example 4-hydroxylauranilide, 4-hydroxystearanilide, octyl N-(3,5-di-tert-butyl-4-hydroxyphenyl)carbamate.

1.12. Esters of β-(3,5-di-tert-butyl-4-hydroxyphenyl)-propionic acid with mono- or polyhydric alcohols, e.g. with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.13. Esters of β-(5-tert-butyl-4-hydroxy-3-methylphenyl)propionic acid with mono- or polyhydric alcohols, e.g. with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14 Esters of β-(3,5-dicyclohexyl-4-hydroxyphenyl)-propionic acid with mono- or polyhydric alcohols, e.g. with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.15 Esters of 3,5-di-tert-butyl-4-hydroxyphenyl acetic acid with mono- or polyhydric alcohols, e.g. with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Amides of β-(3,5-di-tert-butyl-4-hydroxyphenyl)propionic acid e.g. N,N'-bis(3,5-di-tert-butyl-4-hydroxyphenylpropionyl)hexamethylenediamine, N,N'-bis(3,5-di-tert-butyl-4-hydroxyphenylpropionyl)trimethylenediamine, N,N'-bis(3,5-di-tert-butyl-4-hydroxyphenylpropionyl)hydrazine.

2. UV absorbers and light stabilisers 2.1.2-(2'-Hydroxyphenyl)benzotriazoles, for example 2-(2'-hydroxy-5'-methylphenyl)benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chloro-benzotriazole, 2-(3'-tert-butyl-2'-hydroxy-5'-methylphenyl)-5-chloro-benzotriazole, 2-(3'-sec-butyl-5'-tert-butyl-2'-hydroxyphenyl)benzotriazole, 2-(2'-hydroxy-4'-octyloxyphenyl)benzotriazole, 2-(3',5'-di-tert-amyl-2'-hydroxyphenyl)benzotriazole, 2-(3',5'-bis-(α, α-dimethylbenzyl)-2'-hydroxyphenyl)benzotriazole, mixture of 2-(3'-tert-butyl-2'-hydroxy-5'-(2-octyloxycarbonylethyl)phenyl)-5-chloro-benzotriazole, 2-(3'-tert-butyl-5'-[2-(2-ethylhexyloxy)-carbonylethyl]-2'-hydroxyphenyl)-5-chloro-benzotriazole, 2-(3'-tert-butyl-2'-hydroxy-5'-(2-methoxycarbonylethyl)phenyl)-5-chloro-benzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl)phenyl)-benzotriazole, 2-(3'-tert-butyl-5'-[2-(2-ethylhexyloxy)carbonylethyl]-2'-hydroxyphenyl)benzotriazole, 2-(3'-dodecyl-2'-hydroxy-5'-methylphenyl)benzotriazole, and 2-(3'-tert-butyl-2'-hydroxy-5'-(2-isooctyloxycarbonylethyl)phenylbenzotriazole, 2,2'-methylene-bis[4-(1,1,3,3-tetramethylbutyl)-6-benzotriazole-2-ylphenol]; the transesterification product of 2-[3'-tert-butyl-5'-(2-methoxycarbonylethyl)-2'-hydroxyphenyl]-2H-benzotriazole with polyethylene glycol 300; [R—CH$_2$CH$_2$—COO(CH$_2$), where R=3'-tert-butyl-4'-hydroxy-5'-2H-benzotriazol-2-ylphenyl.

2.2. 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, as for example 4-tertbutylphenyl salicylate, phenyl salicylate, octylphenyl salicylate, dibenzoyl resorcinol, bis(4-tert-butylbenzoyl) resorcinol, benzoyl resorcinol, 2,4-di-tertbutylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxycinnamate, butyl α-cyano-β-methyl-p-methoxy-cinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thio-bis-[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenyl undecylketoxime, nickel complexes of 1-phenyl-4-lauroyl-5-hydroxypyrazole, with or without additional ligands.

2.6. Sterically hindered amines, for example bis(2,2,6,6-tetramethyl-piperidyl)sebacate, bis(2,2,6,6-tetramethyl-piperidyl)succinate, bis(1,2,2,6,6-pentamethylpiperidyl)sebacate, bis(1,2,2,6,6-pentamethylpiperidyl) n-butyl-3,5-di-tert-butyl-4-hydroxybenzylmalonate, the condensate of 1-(2-hydroxyethyl)-2,2,6,6-tetramethyl-4-hydroxypiperidine and succinic acid, the condensate of N,N'-bis(2,2,6,6-tetramethyl-4-piperidyl)-hexamethylenediamine and 4-tert-octylamino-2,6-dichloro-1,3,5-triazine, tris(2,2,6,6-tetramethyl-4-piperidyl) nitrilotriacetate, tetrakis(2,2,6,6-tetramethyl-4-piperidyl)-1,2,3,4-butane-tetracarboxylate, 1,1'-(1,2-ethanediyl)bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazaspiro[4.5]decan-2,4-dion, bis(1-octyloxy-2,2,6,6-tetramethylpiperidyl)sebacate, bis(1-octyloxy-2,2,6,6-tetramethylpiperidyl)succinate, the condensate of N,N'-bis-(2,2,6,6-tetramethyl-4-piperidyl)hexamethylenediamine and 4-morpholino-2,6-dichloro-1,3,5-triazine, the condensate of 2-chloro-4,6-bis(4-n-butyl-amino-2,2,6,6-tetramethylpiperidyl )-1,3,5-triazine and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis-(3-aminopropylamino)ethane, 8-acetyl-3-dodecyl-7,7,9,9-tetramethyl-1,3,8-triazaspiro[4.5]-decane-2,4-dione, 3-dodecyl-1-(2,2,6,6-tetramethyl-4-piperidyl)pyrrolidin-2,5-dione, 3-dodecyl-1-(1,2,2,6,6-pentamethyl-4-piperidyl)pyrrolidine-2,5-dione.

2.7. Oxamides, for example 4,4'-dioctyloxyoxanilide, 2,2'-dioctyloxy-5,5'-di-tert-butoxanilide, 2,2'-didodecyloxy-5,5'-di-tert-butoxanilide, 2-ethoxy-2'-ethoxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide and mixtures of ortho- and paramethoxy-disubstituted oxanilides and mixtures of o- and p-ethoxy-disubstituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-[2-hydroxy-4-(2hydroxy-3-butyloxy-propoxy)-phenyl]-4,6-bis(2,4-dimethyl)-1,3,5-triazine, 2-[2-hydroxy-4-(2-hydroxy-3-octyloxy-propyloxy)-phenyl]-4,6-bis(2,4-dimethyl)-1,3,5-triazine.

3. Metal deactivators, for example N,N'-diphenyloxamide, N-salicylal-N'-salicyloyl hydrazine, N,N'-bis(salicyloyl) hydrazine, N,N'-bis(3,5-di-tert-butyl-4-hydroxyphenylpropionyl) hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl)oxalyl dihydrazide, N,N'-bis(salicyloyl)thiopropionyl dihydrazide.

4. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tert-butylphenyl) pentaerythritol diphosphite, bis(2,6-di-tert-butyl-4-methylphenyl)-pentaeryt hritol diphosphite, diisodecyloxypentaerythritol diphosphite, bis(2,4-di-tert-butyl-6-methylphenyl)pentaerythritol diphosphite, bis(2,4,5-tris(tert-butylphenyl)pentaerythritol diphsophite, tristearyl sorbitol triphosphite, tetrakis(2,4-di-tert-butylphenyl) 4,4'-biphenylene diphosphonite, 6-isooctyloxy-2,4,8,10-tetra-tert-butyl-12H-dibenz[d,g]-1,3,2-dioxaphosphocin, 6-fluoro-2,4,8,10-tetra-tert-butyl-12-methyl-dibenz[d,g]-1,3,2-dioxaphosphocin, bis(2,4-di-tert-butyl-6-methylphenyl)methylphosphite, bis(2,4-di-tert-butyl-6-methylphenyl)ethylphosphite.

5. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

6. Polyamide stabilisers, for example, copper salts in combination with iodides and/or phosphorus compounds and salts of divalent manganese.

7. Basic co-stabilisers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example calcium stearate, zinc stearate, magnesium behenate, magnesium stearate, sodium ricinoleate and potassium palmitate, antimony pyrocatecholate or tin pyrocatecholate.

8. Nucleating agents, for example, 4-tert-butylbenzoic acid, adipic acid, diphenylacetic acid.

9. Fillers and reinforcing agents, for example, calcium carbonate, silicates, glass fibres, asbestos, talc, kaolin, mica, barium sulfate, metal oxides and hydroxydes, carbon black, graphite.

10. Other additives, for example, plasticisers, lubricants, emulsifiers, pigments, optical brighteners, flameproofing agents, antistatic agents and blowing agents.

The costabilisers are added, for example, in concentrations of 0.01 to 10%, relative to the total weight of the material to be stabilised.

Incorporation of the compounds of the formula (1) and, if desired, of further additives into the polymeric, organic material is carried out by known methods, for example before or during moulding or else by applying the dissolved or dispersed compounds to the polymeric, organic material, if appropriate with subsequent slow evaporation of the solvent. The compounds of the formula (1) can also be added to the materials to be stabilised in the form of a master batch containing them, for example, in a concentration of 2.5 to 25% by weight.

The compounds of the formula (1) can also be added before and during polymerisation or before crosslinking.

The compounds of the formula (1) can be incorporated into the material to be stabilised in pure form or encapsulated in waxes, oils or polymers.

The compounds of the formula (1) can also be sprayed onto the polymer to be stabilised. They are capable of diluting other additives, for example the abovementioned customary additives (or melts thereof), enabling them also be sprayed onto the polymer to be stabilised together with these additives. Addition by spraying during deactivation of the polymerisation catalysts is particularly advantageous, it being possible, for example, for the steam used for deactivation to be used for spraying.

In the case of bead-polymerised polyolefins, it may be advantageous, for example, to apply the compounds of the formula (1), if appropriate together with other additives, by spraying.

The materials thus stabilised can be used in a wide range of forms, for example as foams, fibres, ribbons, moulded articles, profiles or as binders for paints, adhesives or cement.

The present invention also relates to a process for the stabilisation of an organic material against oxidative, thermal or light-induced degradation, which comprises incorporating therein or applying thereto at least one compound of the formula (1).

As already pointed out, the compounds according to the invention are used particularly advantageously as stabilisers in polyolefins, in particular as heat stabilisers. Excellent stabilisation is obtained, for example, by using them in combination with organic phosphites or phosphonites. In this combination, the compounds according to the invention have the advantage of being effective even in extremely small amounts. They are used, for example, in amounts of 0.0001 to 0.015, in particular 0.0001 to 0.008, % by weight, relative to the polyolefin. The organic phosphite or phosphonite is advantageously used in an amount of 0.01 to 2, in particular 0.01 to 1, % by weight, also relative to the polyolefin. The organic phosphites or phosphonites used are preferably those described in DE-A-4 202 276. See, in particular, the patent claims, the examples and pages 5, last paragraph up to page 11 of that application. Particularly advantageous phosphites and phosphonites can also be seen from item 4 of the above list of co-stabilisers.

The invention also relates to novel compounds of the formula (1),

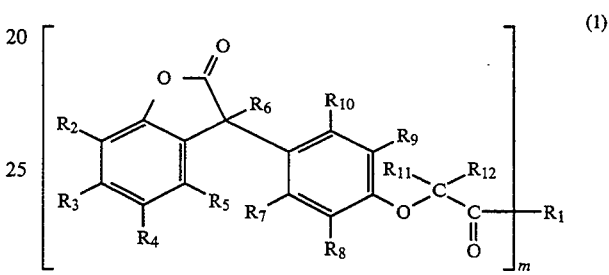

in which $R_2$, $R_3$, $R_4$ and $R_5$, independently of one another, are hydrogen, $C_1$–$C_{25}$alkyl, $C_7$–$C_9$phenylalkyl, unsubstituted or $C_1$–$C_4$alkyl-substituted phenyl, unsubstituted or $C_1$–$C_4$alkyl-substituted $C_5$–$C_8$cycloalkyl; $C_1$–$C_{18}$alkoxy, $C_1$–$C_{25}$alkanoyloxy, $C_3$–$C_{25}$alkenoyloxy, $C_3$–$C_{25}$alkanoyloxy which is interrupted by oxygen, sulfur or $>$N—$R_{13}$; $C_6$–$C_9$cycloalkylcarbonyloxy, benzoyloxy or $C_1$–$C_{12}$alkyl-substituted benzoyloxy, in which $R_{13}$ is hydrogen or $C_1$–$C_8$alkyl, or furthermore the radicals $R_2$ and $R_3$ or the radicals $R_4$ and $R_5$ together with the carbon atoms to which they are bonded form a phenyl ring, $R_4$ is additionally $(CH_2)_n$—$COR_{14}$, in which n is 0, 1 or 2, $R_{14}$ is hydroxyl,

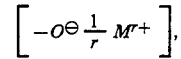

$C_1$–$C_{18}$alkoxy or

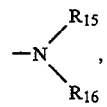

$R_{15}$ and $R_{16}$, independently of one another, are hydrogen or $C_1$–$C_{18}$alkyl, M is an r-valent metal cation and r is 1, 2 or 3, $R_7$, $R_8$, $R_9$ and $R_{10}$, independently of one another, are hydrogen, $C_1$–$C_4$alkyl or $C_1$–$C_4$alkoxy, with the proviso that at least one of the radicals $R_7$, $R_8$, $R_9$ and $R_{10}$ is hydrogen, $R_{11}$ and $R_{12}$, independently of one another, are hydrogen, $C_1$–$C_4$alkyl or phenyl, and, in the case where $R_3$, $R_5$, $R_6$, $R_7$ and $R_{10}$ are hydrogen, $R_4$ is additionally a radical of the formula (2),

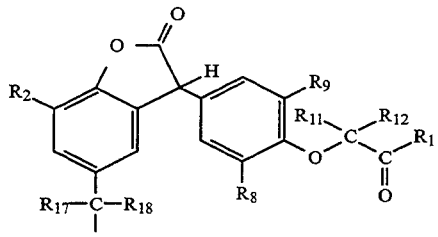

in which $R_2$, $R_8$, $R_9$, $R_{11}$ and $R_{12}$ are as defined above and $R_1$ is as defined below for $m=1$ and $R_{17}$ and $R_{18}$, independently of one another, are hydrogen, $C_1$-$C_{12}$alkyl or phenyl, or $R_{17}$ and $R_{18}$ together with the carbon atom to which they are bonded form a $C_5$-$C_7$cycloalkylidene ring which is unsubstituted or substituted by 1 to 3 $C_1$-$C_4$alkyl, m is an integer from the range of 1 to 6, and, in the case where m is 1, $R_1$ is hydroxyl, $C_1$-$C_{30}$alkoxy, $C_3$-$C_{30}$alkoxy which is interrupted by oxygen, sulfur or $>$N—$R_{13}$; $C_7$-$C_9$phenylalkoxy, $C_5$-$C_{12}$cycloalkoxy, $C_2$-$C_{18}$alkenyloxy, unsubstituted or $C_1$-$C_{12}$alkyl-substituted phenoxy,

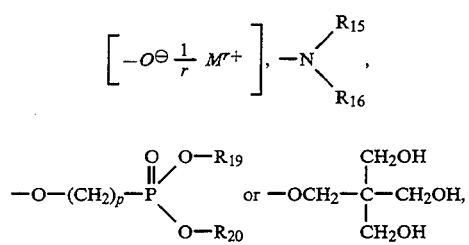

$R_{13}$, $R_{15}$, $R_{16}$, r and M are as defined above, $R_{19}$ and $R_{20}$, independently of one another, are $C_1$-$C_4$alkyl, p is 1 or 2, and $R_6$ is hydrogen or a radical of the formula (3),

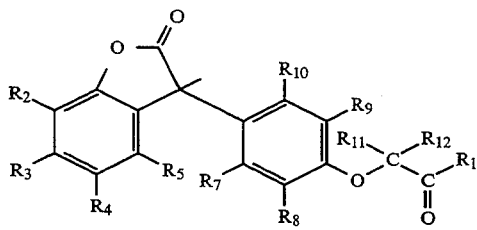

in which $R_1$, $R_2$, $R_3$, $R_4$, $R_5$, $R_7$, $R_8$, $R_9$, $R_{10}$, $R_{11}$ and $R_{12}$ are as defined above; or, in the case where m is 2, $R_1$ is $C_2$-$C_{12}$alkanedioxy, $C_3$-$C_{25}$alkanedioxy which is interrupted by oxygen, sulfur or $>$N—$R_{13}$,

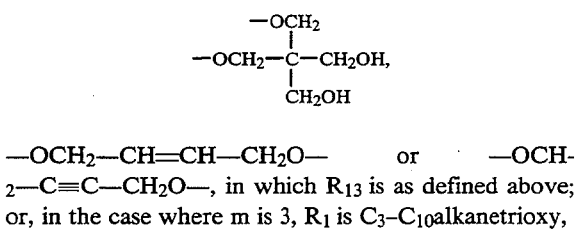

—OCH$_2$—CH=CH—CH$_2$O—  or  —OCH$_2$—C≡C—CH$_2$O—, in which $R_{13}$ is as defined above; or, in the case where m is 3, $R_1$ is $C_3$-$C_{10}$alkanetrioxy,

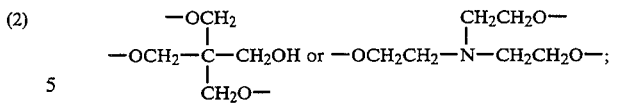

or, in the case where m is 4, $R_1$ is $C_1$-$C_4$alkanetetraoxy,

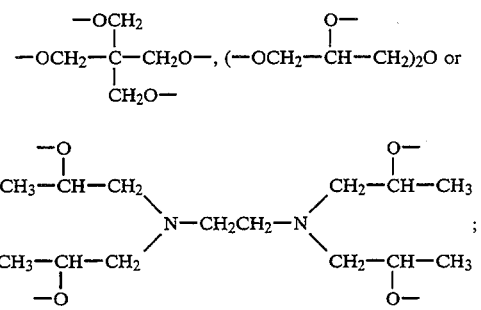

or, in the case where m is 5, $R_1$ is $C_5$-$C_{10}$alkanepentaoxy; or in the case where m is 6, $R_1$ is $C_6$-$C_{10}$alkanehexaoxy or

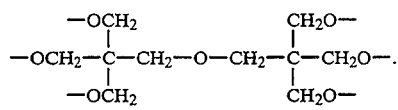

Preferred groups of novel compounds of the formula (1) conform to the preferences expressed above for the compositions according to the invention.

Preference is also given to compounds of the formula (1) in which $R_2$, $R_3$, $R_4$ and $R_5$, independently of one another, are hydrogen, $C_1$-$C_{18}$alkyl, benzyl, phenyl, $C_5$-$C_8$cycloalkyl, $C_1$-$C_8$alkoxy, $C_1$-$C_{18}$alkanolyoxy, $C_3$-$C_{18}$alkenoyloxy or benzoyloxy, $R_4$ is additionally —(CH$_2$)$_n$—COR$_{14}$, m is 1 to 4, and, in the case where m is 1, $R_1$ is hydroxyl, $C_1$-$C_{18}$alkoxy, $C_3$-$C_{18}$alkoxy which is interrupted by oxygen, sulfur or $>$N—$R_{13}$; benzyloxy, $C_5$-$C_8$cycloalkoxy, unsubstituted or $C_1$-$C_8$alkyl-substituted phenoxy,

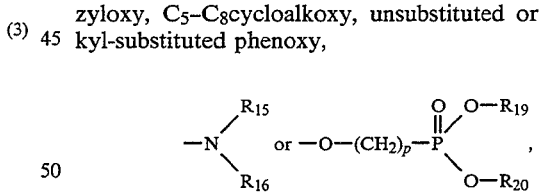

$R_{13}$, $R_{15}$, $R_{16}$, p, $R_{19}$ and $R_{20}$ being as defined above; or, in the case where m is 2, $R_1$ is $C_2$-$C_{12}$alkanedioxy or $C_3$-$C_{25}$alkanedioxy which is interrupted by oxygen; or, in the case where m is 3, $R_1$ is $C_3$-$C_{10}$alkanetrioxy; or, in the case where m is 4, $R_1$ is

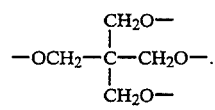

Preference is also given to compounds of the formula (1) in which at least two of the radicals $R_2$, $R_3$, $R_4$ and $R_5$ are hydrogen.

Particular preference is given to compounds of the formula (1) in which $R_3$ and $R_5$ are hydrogen.

Preference is also given to compounds of the formula (1) in which m is 1.

Of particular interest are compounds of the formula (1) in which m is 1, $R_1$ is hydroxyl, $C_1$-$C_{18}$alkoxy, $C_3$-$C_{18}$alkoxy which is interrupted by oxygen, unsubstituted or $C_1$-$C_8$alkyl-substituted phenoxy,

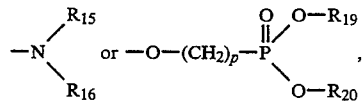

$R_{15}$ and $R_{16}$, independently of one another, being hydrogen or $C_1$-$C_{12}$alkyl, $R_2$ is hydrogen, $C_1$-$C_{18}$alkyl or cyclohexyl, $R_3$, $R_5$, $R_7$ and $R_{10}$ are hydrogen, or the radicals $R_2$ and $R_3$ together with the carbon atoms to which they are bonded form a phenyl ring, $R_4$ is hydrogen, $C_1$-$C_6$alkyl, cyclohexyl, $C_1$-$C_4$alkoxy or —(CH$_2$)$_2$—COR$_{14}$, in which $R_{14}$ is $C_1$-$C_4$alkyl, $R_8$, $R_9$, $R_{11}$ and $R_{12}$, independently of one another, are hydrogen or $C_1$-$C_4$alkyl, and, in the case where $R_6$ is hydrogen, $R_4$ is additionally a radical of the formula (2),

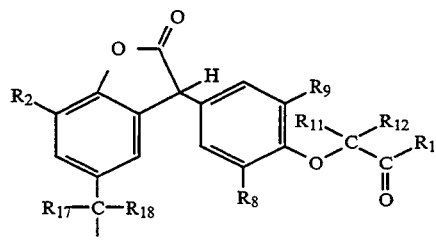 (2)

in which $R_1$, $R_2$, $R_8$, $R_9$, $R_{11}$ and $R_{12}$ are as defined above, $R_{17}$ and $R_{18}$, independently of one another, are hydrogen or $C_1$-$C_4$alkyl, or $R_{17}$ and $R_{18}$ together with the carbon atom to which they are bonded form a $C_5$-$C_7$cycloalkylidene ring, $R_6$ is hydrogen of a radical of the formula (3),

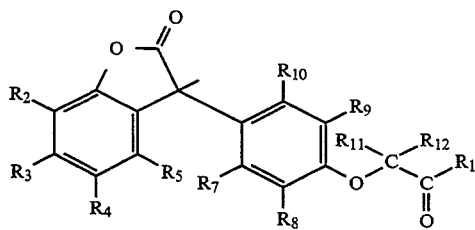 (3)

in which $R_1$, $R_2$, $R_3$, $R_4$, $R_5$, $R_7$, $R_8$, $R_9$, $R_{10}$, $R_{11}$ and $R_{12}$ are as defined above.

Specific preference is given to compounds of the formula (1) in which m is 1, $R_1$ is hydroxyl, $C_1$-$C_{18}$alkoxy, unsubstituted or $C_1$-$C_4$alkyl-substituted phenoxy;

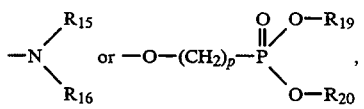

$R_{15}$ and $R_{16}$, independently of one another, being hydrogen or $C_1$-$C_4$alkyl, p being 1 or 2 and $R_{19}$ and $R_{20}$ being $C_1$-$C_4$alkyl, $R_2$ is hydrogen or $C_1$-$C_{18}$alkyl, $R_3$, $R_5$, $R_7$, $R_{10}$, $R_{11}$ and $R_{12}$ are hydrogen, $R_4$ is hydrogen or $C_1$-$C_4$alkyl, and in the case where $R_6$ is hydrogen, $R_4$ is additionally a radical of the formula (2),

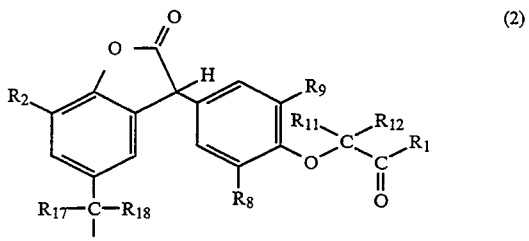 (2)

$R_{17}$ and $R_{18}$ together with the carbon atom to which they are bonded form a cyclohexylidene ring, $R_8$ and $R_9$, independently of one another, are hydrogen or $C_1$-$C_4$alkyl, $R_6$ is hydrogen or a radical of the formula (3),

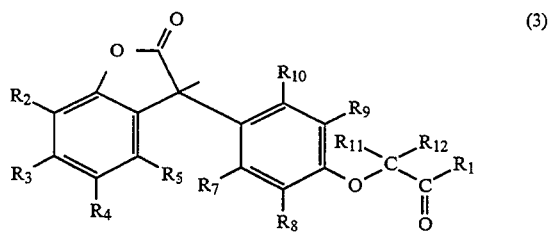 (3)

in which $R_1$, $R_2$, $R_3$, $R_4$, $R_5$, $R_7$, $R_8$, $R_9$, $R_{10}$, $R_{11}$ and $R_{12}$ are as defined above.

The compounds according to the invention of the formula (1) can be prepared in a manner known per se.

For example, this being the preferred procedure, a phenol of the formula (4),

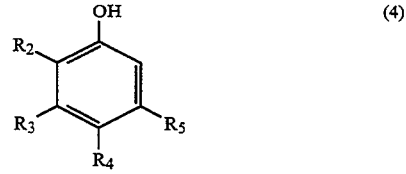 (4)

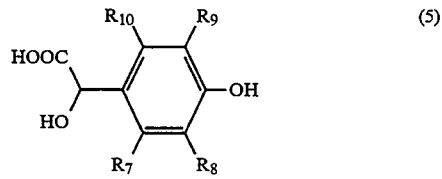 (5)

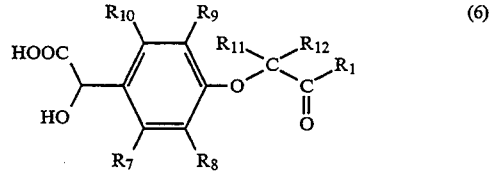 (6)

in which $R_2$, $R_3$, $R_4$ and $R_5$ are as defined, are reacted with a mandelic acid which is substituted on the phenyl ring and has the formula (5) or (6), in which $R_1$, $R_7$, $R_8$, $R_9$, $R_{10}$, $R_{11}$ and $R_{12}$ are as defined, at elevated temperature, in particular at temperatures of from 130° to 200° C., in the melt or in a solvent, if appropriate under a slight vacuum. The reaction is preferably carried out in a solvent, for example acetic acid or formic acid in a temperature range of from 50° to 130° C. The reaction can be catalysed by addition of an acid, such as hydrochloric acid, sulfuric acid or methanesulfonic acid. The reaction can be carried out, for example, in the manner described in the references given in the introduction of the description.

The 4-hydroxymandelic acids which are substituted on the phenyl ring and have the formula (5) are known in the literature or can be prepared analogously, for example, as described by W. Bradley et al., J. Chem. Soc. 1956, 1622; EP-A-146 269 or DE-A-2 944 295.

The 4-carboxymethoxymandelic acids which are substituted on the phenyl ring and have the formula (6), in which $R_1$ is hydroxyl, can be prepared by generally known etherification conditions starting with the phenols of the formula (5), for example in accordance with Organikum 1986, page 194–200, for example by alkylation with an α-chloroacetic acid derivative of the formula

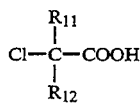

under basic conditions.

The phenols of the formula (4) are also known or can be obtained by methods known per se.

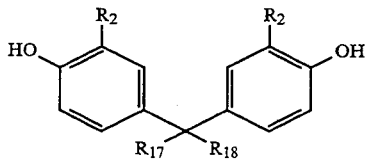

Bisphenol compounds of the formula (7) can be prepared according to Houben-Weyl, Methoden der organischen Chemie (Methods of Organic Chemistry), Volume 6/1c, 1030.

The 3-(carboxymethoxyphenyl)benzofuran-2-ones obtained by this reaction and having the formula (1), in which $R_1$ is hydroxyl and m is 1, can be derivatised by generally known esterification and amidation methods, for example according to Organikum 1986, page 402–410, with m-hydric alcohols of the formula $R_1{}^1(OH)_m$, in which $R_1{}^1(O)_m$ is $R_1$ without hydroxyl and m is an integer from the range of from 1 to 6, or with primary or secondary amines of the formula

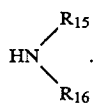

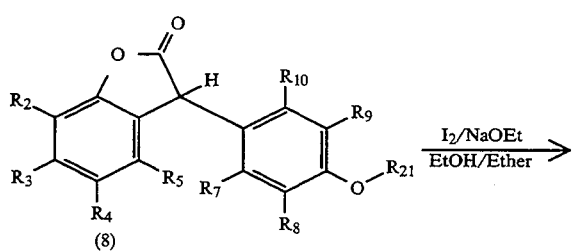

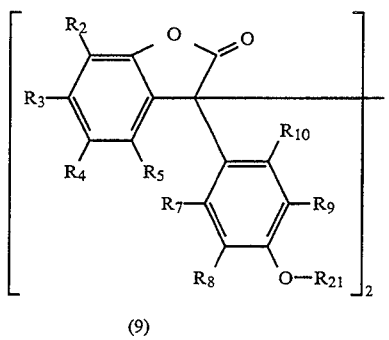

Dimerisation of the compounds of the formula (8), in which $R_{21}$ is the formula

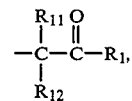

to prepare compounds of the formula (1) in which $R_6$ is a group of the formula (3) [compounds of the formula (9)] takes place by oxidation with, for example, iodine under basic conditions in an organic solvent at room temperature. A suitable base is in particular sodium ethoxide, and suitable solvents are ethanol and diethyl ether.

The examples which follow illustrate the invention further. Parts or percentages given are by weight.

EXAMPLE 1 a) Preparation of 3-(4-carboxymethoxyphenyl)-5-methylbenzofuran-2-one (Compound (101), Table 1).

A mixture of 41.6 g (0.39 mol) of p-cresol and 29.0 g (0.13 mol) of 4-carboxymethoxymandelic acid is maintained at 185° C. under a nitrogen atmosphere for 90 minutes, during which the water formed is distilled off. Excess p-cresol is then distilled off under reduced pressure. Crystallisation of the residue from 75 ml of xylene gives 31.4 g (81%) of 3-(4-carboxymethoxyphenyl)-5-methylbenzofuran-2-one, melting point 198°–203° C. (compound (101), Table 1).

Compounds (102) and (103) are prepared analogously to Example 1 from the substituted mandelic acids described in the following section.

b) Preparation of 4-carboxymethoxy-3-methylmandelic acid.

4.7 g (0.05 mol) of chloroacetic acid is added to a solution of 9.11 g (0.05 mol) of 4-hydroxy-3-methylmandelic acid and 6.0 g (0.15 mol) of sodium hydroxide in 25 ml of water, and the mixture is then stirred at 80° C. for 3 hours. The reaction mixture is acidified with concentrated hydrochloric acid, cooled with ice/water, and the precipitated product is filtered, washed with water and dried in a high vacuum, giving 5.65 g (62%) of 4-carboxymethoxy-3-methylmandelic acid, melting point 95°–100° C.

4-Carboxymethoxy-3,5-dimethylmandelic acid, melting point 150°–152° C., is obtained analogously to Example 1b) from 3,5-dimethyl-4-hydroxymandelic acid in a yield of 60%.

c) Preparation of 4-hydroxy-3-methylmandelic acid.

32.4 g (0.30 mol) of o-cresol are dissolved in 150 ml of 2N sodium hydroxide solution under a nitrogen atmosphere. After cooling to +5° C., 4.8 g (0.12 mol) of sodium hydroxide and 13.3 ml (0.12 mol) of 50% aqueous glycolic acid are added, and the reaction mixture is stirred at room temperature for 4 hours. A further 0.12 mol of sodium hydroxide and glycolic acid (a total of 0.36 mol) is added twice after 4 hours each time. The reaction mixture is then stirred for another 12 hours, neutralised with concentrated hydrochloric acid and washed twice with 75 ml of petroleum ether. The aqueous phase is then acidified with concentrated hydrochloric acid and extracted several times with ether. The organic phases are combined, dried over magnesium sulfate and concentrated on a vacuum rotary evaporator, giving 30.1 g (55%) of 4-hydroxy-3-methylmandelic acid, melting point 115°–120° C.

EXAMPLE 2

Preparation of 5-methyl-3-(4-n-octadecyloxycarbonylmethoxyphenyl)benzofuran-2-one (Compound (105), Table 1).

A mixture of 5.0 g (18.5 mmol) of 1-octadecanol, 5.0 g (16.8 mmol) of 3-(4-carboxymethoxyphenyl)-5-methylbenzofuran-2-one (Compound (101), Example 1) and 1.0 g (5.3 mmol) of p-toluenesulfonic acid is stirred at 200° C. under a slight vacuum (150 mmHg) for about 1 hour. The reaction mixture is then diluted with 60 ml of ligroin and cooled with ice/water. The precipitated product is filtered. Crystallisation of the residue due from ligroin given 7.5 g (81%) of 5-methyl-3-(4-n-octadecyloxycarbonylmethoxyphenyl)benzofuran-2-one, melting pint 85°–87° C. (Compound (105), Table 1).

Compounds (104), (107) and (108) are prepared analogously to Example 2 from the corresponding benzofuran-2-ones and alcohols.

EXAMPLE 3

Preparation of 5,7-dimethyl-3-(4-n-octadecyloxycarbonylmethoxyphenyl)benzofuran-2-one (Compound (109), Table 1).

A mixture of 18.3 g (0.15 mol) of 2,4-dimethylphenol and 11.3 g (0.05 mol) of 4-carboxymethoxymandelic acid is stirred at about 185° C. for 3.5 hours. Excess 2,4-dimethylphenol is then distilled off in a high vacuum. 12.5 g (0.046 mol) of 1-octadecanol and 0.3 g (1.58 mmol) of p-toluenesulfonic acid are added to the residue, and the mixture is maintained at about 185° C. under a slight vacuum (50 mbar) for 1.5 hours. The reaction mixture is diluted with 50 ml of toluene and washed with water. The organic phases are combined, dried over magnesium sulfate and concentrated on a vacuum rotary evaporator. Crystallisation of the residue from acetonitrile gives 9.9 g (38%) of 5,7-dimethyl-3-(4-n-octadecyloxycarbonylmethoxyphenyl)benzofuran-2-one, melting point 57°–59° C. (Compound (109), Table 1).

Compound (110) is prepared analogously to Example 3 from the corresponding benzofuran-2-one.

EXAMPLE 4

A solution of 6.0 g (20.0 mmol) of 3-(4-carboxymethoxyphenyl)-5-methylbenzofuran-2-one (Compound (101), Example 1), 4.12 g (20.0 mmol) of N,N'-dicyclohexylcarbodiimide, 0.1 g (0.82 mmol) of 4-dimethylaminopyridine and 3.36 g (21.8 mmol) of dimethyl hydroxyethylphosphonate in 50 ml of absolute dichloromethane is stirred at room temperature for 2.5 hours. The reaction mixture is filtered, and the filtrate is chromatographed on silica gel using the eluent system dichloromethane/ethyl acetate (3:2), giving 7.30 g (84%) of the oily compound (111) (Table 1).

Compound (112) is obtained analogously to Example 4 from the diethyl hydroxymethylphosphonate.

EXAMPLE 5

A mixture of 6.95 g (64.3 mmol) of p-cresol and 4.83 g (21.4 mmol) of 4-carboxymethoxymandelic acid is maintained at about 185° C. under a nitrogen atmosphere for 2.5 hours. Excess p-cresol is then distilled off under reduced pressure. 6.3 g (42 mmol) of p-cresol acetate and 50 mg of dibutyltin oxide are added to the residue. The reaction mixture is maintained at 180° C. under a slight vacuum (600 mbar) for 4 hours. Excess p-cresol acetate is distilled off in a high vacuum. Chromatography of the residue on silica gel using the eluent system dichloromethane/hexane (3:1) and crystallisation of the pure fractions from methanol give 2.3 g (28%) of Compound (106) (Table 1), melting point 139°–142° C.

EXAMPLE 6

A mixture of 10.3 g (50 mmol) of 2,4-di-tert-butylphenol, 11.3 g (50 mmol) of 4-carboxymethoxymandelic acid and 0.5 g (5.2 mmol) of methanesulfonic acid in 25 ml of acetic acid is refluxed for 4 hours. The acetic acid is then distilled off, 50 ml of ethanol is added to the residue, and the mixture is refluxed for 2 hours in an apparatus fitted with a tube containing molecular sieve. The reaction mixture is concentrated, and the residue is diluted with toluene and washed with dilute sodium bicarbonate solution. The organic phases are combined, dried over magnesium sulfate and concentrated on a vacuum rotary evaporator. Crystallisation of the residue from ligroin gives 16.1 g (76%) of Compound (113), melting point 95°–96° C. (Table 1).

Compounds (114) and (120) are prepared analogously to Example 6 from the corresponding phenols. To prepare Compound (120), 2 equivalents of 4-carboxymethoxymandelic acid are used per bisphenol used.

EXAMPLE 7

A mixture of 5.0 g (11.8 mmol) of 5,7-di-tert-butyl-3-(4-ethoxycarbonylmethoxyphenyl)benzofuran-2-one (Compound (113), Example 6) and 2 g of strong acidic ion exchanger (Dowex) in 50 ml of methanol is refluxed for 4 hours. The reaction mixture is filtered, and the filtrate is concentrated on a vacuum rotary evaporator. Crystallisation of the residue from ligroin gives 3.0 g (62%) of 5,7-di-tert-butyl-3-(4-methoxycarbonylmethoxyphenyl)benzofuran-2-one, melting point 115°–117° C. (Compound (115), Table 1).

EXAMPLE 8

A mixture of 20.6 g (0.10 mol) of 2,4-di-tert-butylphenol, 22.6 g (0.10 mol) of 4-carboxymethoxymandelic acid and 1 g (10 mmol) of methanesulfonic acid in 50 ml of acetic acid is refluxed for 15 hours. The acetic acid is then distilled off. The residue is dissolved in 100 ml of dichloromethane, and the solution is washed three times with water. The organic phases are combined, dried over magnesium sulfate and concentrated on a vacuum rotary evaporator. Crystallisation of the residue from ligroin gives 31.0 g (78%) of 5,7-di-tert-butyl-3-(4-carboxymethoxyphenyl)benzofuran-2-one, melting point 158°–162° C. (Compound (116), Table 1).

EXAMPLE 9

A mixture of 7.93 g (20 mmol) of 5,7-di-tert-butyl-3-(4-carboxymethoxyphenyl)benzofuran-2-one (Compound (116), Example 8), 4.13 g (20.0 mmol) of N,N'-dicyclohexylcarbodiimide, 120 mg (1.0 mmol) of 4-dimethylaminopyridine and 2.6 g (35.5 mmol) of di-n-butylamine in 50 ml of dichloromethane is stirred at room temperature for 2 hours. The reaction mixture is filtered, and the filtrate is concentrated on a vacuum rotary evaporator. Chromatography of the residue on silica gel using the eluent system ethyl acetate/hexane (5:1) gives 5.4 g (53%) of Compound (117) (Table 1) in the form of a resin.

Compound (118) is prepared analogously to Example 9 starting with n-butylamine.

EXAMPLE 10

Preparation of 3,3'-bis[5,7-di-tert-butyl-3-(4-ethoxycarbonylmethoxyphenyl)benzofuran-2-one] (Compound (119), Table 1).

17.0 g (40.0 mmol) of 5,7-di-tert-butyl-3-(4-ethoxycarbonylmethoxyphenyl)benzofuran-2-one (Compound (113), Example 6) are added under a nitrogen atmosphere to a sodium ethoxide solution prepared by addition of 0.92 g (40.0 mmol) of sodium to 80 ml of absolute ethanol. A solution of 5.10 g (40.0 mmol) of iodine in 50 ml of diethyl ether is then added dropwise at room temperature over a period of about 10 minutes. The reaction mixture is stirred for another 1.5 hours, then diluted with 250 ml of water and extracted with dichloromethane. The organic phases are separated off, washed with water, combined, dried over magnesium sulfate and concentrated on a vacuum rotary evaporator. Two crystallisations of the residue from ethanol give 2.88 g (17%) of 3,3'-bis[5,7-di-tert-butyl-3-(4-ethoxycarbonyl-methoxyphenyl)benzofuran-2-one], melting point 180°–185° C. (Compound (119), Table 1).

TABLE 1

| No. | Compound | M.p. (°C.) | C(%), H(%), N(%) (calculated/found) | Yield (%) |
|---|---|---|---|---|
| 101 | [structure] | 198–203 | 68.45 4.73 / 68.13 4.86 | 81 |
| 102 | [structure] | 195–198 | Characterised by $^1$H NMR in DMF-$d_7$ δ(H*) = 5.23 ppm | 90 |
| 103 | [structure] | 175–180 | 69.93 5.56 / 69.96 5.73 | 71 |
| 104 | [structure] | 69–70 | 74.65 8.21 / 74.67 8.10 | 61 |

TABLE 1-continued
| No. | Compound | M.p. (°C.) | C(%), H(%), N(%) (calculated/found) | Yield (%) |
|---|---|---|---|---|
| 105 | 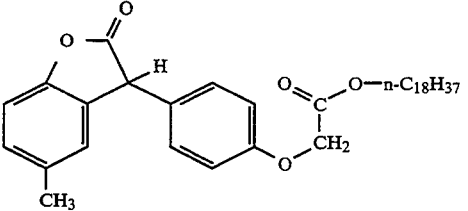 | 85–87 | 76.33 9.15<br>76.38 9.26 | 81 |
| 106 | 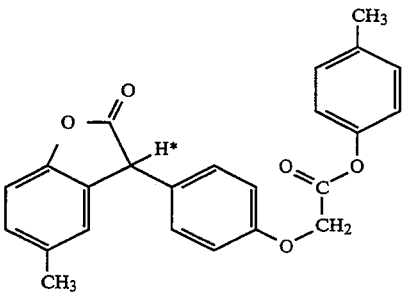 | 139–142 | Characterised by $^1$H NMR in CDCl$_3$ δ(H*) = 4.82 ppm | 28 |
| 107 | 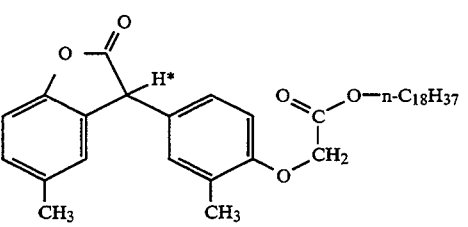 | 96–97 | Characterised by $^1$H NMR in CDCl$_3$ δ(H*) = 4.75 ppm | 81 |
| 108 | 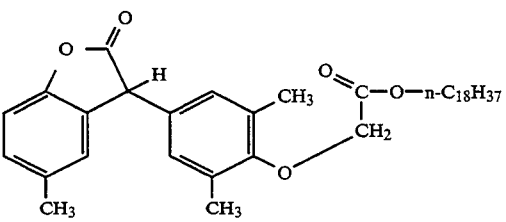 | 84–86 | 76.78 9.40<br>76.89 9.53 | 64 |
| 109 | 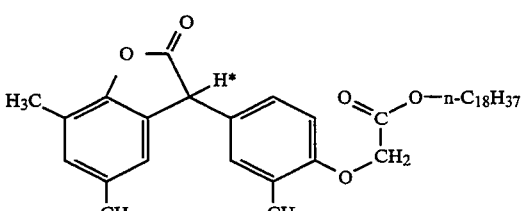 | 57–59 | Characterised by $^1$H NMR in CDCl$_3$ δ(H*) = 4.80 ppm | 38 |
| 110 | 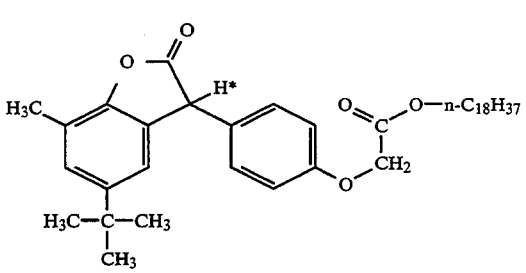 | Oil | Characterised by $^1$H NMR in CDCl$_3$ δ(H*) = 4.82 ppm | 60 |

TABLE 1-continued

| No. | Compound | M.p. (°C.) | C(%), H(%), N(%) (calculated/found) | Yield (%) |
|---|---|---|---|---|
| 111 | (structure) | Oil | Characterised by $^1$H NMR in CDCl$_3$ δ(H*) = 4.80 ppm | 84 |
| 112 | (structure) | Resin | Characterised by $^1$H NMR in CDCl$_3$ δ(H*) = 4.80 ppm | 78 |
| 113 | (structure) | 95–96 | 73.56  7.60<br>73.42  7.64 | 76 |
| 114 | (structure) | Resin | 76.78  9.40<br>76.85  9.59 | 39 |
| 115 | (structure) | 115–117 | 73.15  7.37<br>73,27  7,46 | 62 |
| 116 | (structure) | 158–162 | 72.71  7.12<br>72.59  7.41 | 78 |

TABLE 1-continued

| No. | Compound | M.p. (°C.) | C(%), H(%), N(%) (calculated/found) | Yield (%) |
|---|---|---|---|---|
| 117 | (structure: 3,5-di-tert-butyl-2-methylphenyl / phenyl / OCH₂C(O)N(n-C₄H₉)₂) | Resin | 75.70  8.93  2.76<br>75.43  8.82  3.06 | 53 |
| 118 | (structure: 3,5-di-tert-butyl-2-methylphenyl / phenyl / OCH₂**C(O)NH-n-C₄H₉) with H* | Resin | Characterised by<br>¹H NMR in CDCl₃<br>δ(H*) = 4.80 ppm<br>δ(H**) = 4.48 ppm | 47 |
| 119 | [bis structure with OCH₂CO₂CH₂CH₃]₂ | 180–185 | 73.73  7.38<br>73.74  7.44 | 17 |
| 120 | (bis-phenyl cyclohexylidene-bridged structure with CH₃CH₂O₂CCH₂O* and *OCH₂CO₂CH₂CH₃) | Resin | Characterised by<br>¹H NMR in CDCl₃<br>δ(H*) = 4.60 ppm | 11 |

EXAMPLE 11

Stabilisation of polypropylene in multiple extrusion.

1.3 kg of polypropylene powder (Profax 6501) which is prestabilised with 0.025% of Irganox® 1076 n-octadecyl (3-[3,5-di-tert-butyl-4-hydroxyphenyl]propionate) (having a melt index of 3.2 measured at 230° C. and on 2.16 kg) are mixed with 0.05% of Irganox® 1010 (pentaerythritol tetrakis[3-(3,5-di-ten-butyl-4-hydroxyphenyl)propionate]), 0.05% of calcium stearate, 0.03% of dihydrotalcite (DHT 4A, Kyowa Chemical Industry Co., Ltd., [Mg$_{4.5}$Al$_2$(OH)$_{13}$CO$_3$.3,5 H$_2$O]) and 0.015% of the compound from Table 1. This mixture is extruded in an extruder having a cylinder diameter of 20 mm and a length of 400 mm at 100 revolutions per minute, the 3 heating zones being set at the following temperatures: 260°, 270°, 280° C. For cooling, the extrudate is passed through a water bath and then granulated. These granules are repeatedly extruded. After 3 extrusions, the melt index is measured (at 230° C. on 2.16 kg). A large increase in the melt index indicates extensive chain degradation, that is poor stabilisation. The results are summarised in Table 2.

TABLE 2

| Compound from Table 1 | Melt index after 3 extrusions |
|---|---|
| — | 20.0 |
| 106 | 7.4 |
| 107 | 7.6 |
| 110 | 7.0 |

EXAMPLE 12

Stabilisation of polyethylene during processing.

100 parts of polyethylene powder (Lupolen 5260 Z) are mixed with 0.05 part of pentaerythritol tetrakis[3-(3,5-di-tert-butyl-4-hydroxyphenyl)propionate], 0.05 part of tris(2,4-di-tert-butylphenyl) phosphite and 0.05 part of the compound from Table 1, and the mixture is kneaded in a Brabender plastograph at 220° C. and 50 revolutions per minute. During this time, the kneading resistance is continuously recorded as torque. In the course of kneading, the polymer, after remaining unchanged for an extended period of time, starts to crosslink, which can be detected by a rapid increase in torque. In Table 3, the time until torque shows a substantial increase is given as a measure of the stabiliser effect. The longer this time, the better the stabiliser effect.

TABLE 3

| Compound from Table 1 | Time until torque increases (min) |
|---|---|
| — | 9.0 |
| 105 | 29.5 |
| 106 | 33.0 |
| 107 | 30.0 |
| 110 | 30.0 |
| 111 | 27.0 |
| 112 | 28.5 |

What is claimed is:

1. A composition comprising
a) an organic material subject to oxidative, thermal or light-induced degradation and
b) at least one compound of the formula (1),

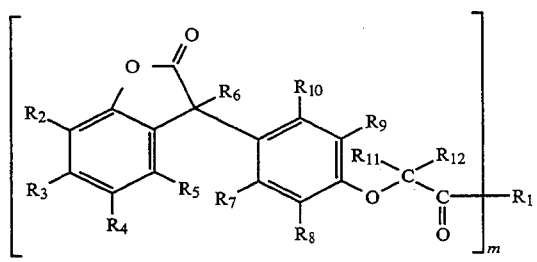

in which $R_2$, $R_3$, $R_4$ and $R_5$, independently of one another, are hydrogen, $C_1$-$C_{25}$alkyl, $C_7$-$C_9$phenylalkyl, unsubstituted or $C_1$-$C_4$alkyl-substituted phenyl, unsubstituted or $C_1$-$C_4$alkyl-substituted $C_5$-$C_8$cycloalkyl; $C_1$-$C_{18}$alkoxy, hydroxyl, $C_1$-$C_{25}$alkanoyloxy, $C_3$-$C_{25}$alkenoyloxy, $C_3$-$C_{25}$alkanoyloxy which is interrupted by oxygen, sulfur or >N—$R_{13}$; $C_6$-$C_9$cycloalkylcarbonyloxy, benzoyloxy or $C_1$-$C_{12}$alkyl-substituted benzoyloxy, in which $R_{13}$ is hydrogen or $C_1$-$C_8$alkyl, or furthermore the radicals $R_2$ and $R_3$ or the radicals $R_4$ and $R_5$ together with the carbon atoms to which they are bonded form a phenyl ring, $R_4$ is additionally (CH$_2$)$_n$—COR$_{14}$, in which n is 0, 1 or 2, $R_{14}$ is hydroxyl,

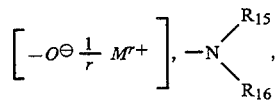

$C_1$-$C_{18}$alkoxy or

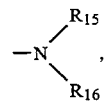

$R_{15}$ and $R_{16}$, independently of one another, are hydrogen or $C_1$-$C_{18}$alkyl, M is an r-valent metal cation and r is 1, 2 or 3, $R_7$, $R_8$, $R_9$ and $R_{10}$, independently of one another, are hydrogen, $C_1$-$C_4$alkyl or $C_1$-$C_4$alkoxy, with the proviso that at least one of the radicals $R_7$, $R_8$, $R_9$ and $R_{10}$ is hydrogen, $R_{11}$ and $R_{12}$, independently of one another, are hydrogen, $C_1$-$C_4$alkyl or phenyl, and, in the case where $R_3$, $R_5$, $R_6$, $R_7$ and $R_{10}$ are hydrogen, $R_4$ is additionally a radical of the formula (2),

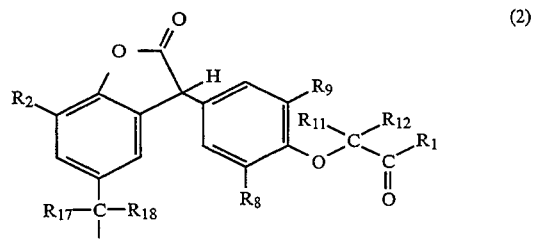

in which $R_2$, $R_8$, $R_9$, $R_{11}$ and $R_{12}$ are as defined above and $R_1$ is as defined below for m=1 and $R_{17}$ and $R_{18}$, independently of one another, are hydrogen, $C_1$-$C_{12}$alkyl or phenyl, or $R_{17}$ and $R_{18}$ together with the carbon atom to which they are bonded form a $C_5$-$C_7$cycloalkylidene ring which is unsubstituted or substituted by 1 to 3 $C_1$-$C_4$alkyl, m is an integer from the range of 1 to 6, and, in the case where m is 1, $R_1$ is hydroxyl, $C_1$-$C_{30}$alkoxy, $C_3$-$C_{30}$alkoxy which is interrupted by oxygen, sulfur or >N—$R_{13}$; $C_7$-$C_9$phenylalkoxy, $C_5$-$C_{12}$cycloalkoxy, $C_2$-$C_{18}$alkenyloxy, unsubstituted or $C_1$-$C_{12}$alkyl-substituted phenoxy,

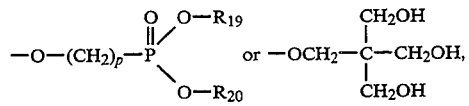

$R_{13}$, $R_{15}$, $R_{16}$, r and M are as defined above, $R_{19}$ and $R_{20}$, independently of one another, are $C_1$-$C_4$alkyl, p is 1 or 2, and $R_6$ is hydrogen or a radical of the formula (3),

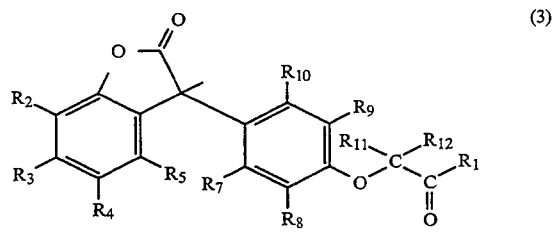

in which $R_1$, $R_2$, $R_3$, $R_4$, $R_5$, $R_7$, $R_8$, $R_9$, $R_{10}$, $R_{11}$ and $R_{12}$ are as defined above; or in the case where m is 2, $R_1$ is $C_2$-$C_{12}$alkanedioxy, $C_3$-$C_{25}$alkanedioxy which is interrupted by oxygen, sulfur or $>N-R_{13}$;

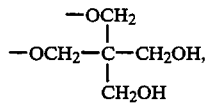

$-OCH_2-CH=CH-CH_2O-$ or $-OCH_2-C\equiv C-CH_2O-$, in which $R_{13}$ is as defined above; or, in the case where m is 3, $R_1$ is $C_3$-$C_{10}$alkanetrioxy,

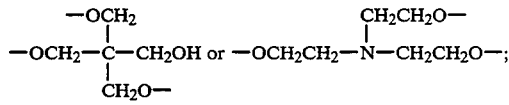

or, in the case where m is 4, $R_1$ is $C_4$-$C_{10}$alkanetetraoxy,

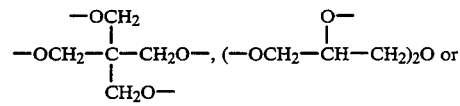

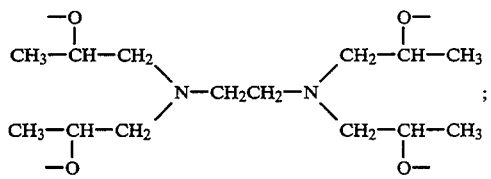

or, in the case where m is 5, $R_1$ is $C_5$-$C_{10}$alkanepentaoxy; or in the case where m is 6, $R_1$ is $C_6$-$C_{10}$alkanehexaoxy or

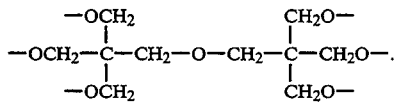

2. A composition according to claim 1, in which $R_2$, $R_3$, $R_4$ and $R_5$, independently of one another, are hydrogen, $C_1$-$C_{18}$alkyl, benzyl, phenyl, $C_5$-$C_8$cycloalkyl, $C_1$-$C_8$alkoxy, hydroxyl, $C_1$-$C_{18}$alkanoyloxy, $C_3$-$C_{18}$alkenoyloxy or benzoyloxy, $R_4$ is additionally $-(CH_2)_n-COR_{14}$, m is 1 to 4, and, in the case where m is 1, $R_1$ is hydroxyl, $C_1$-$C_{18}$alkoxy, $C_3$-$C_{18}$alkoxy which is interrupted by oxygen, sulfur or $>N-R_{13}$; benzyloxy, $C_5$-$C_8$cycloalkoxy, unsubstituted or $C_1$-$C_8$alkyl-substituted phenoxy,

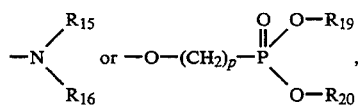

$R_{13}$, $R_{15}$, $R_{16}$, p, $R_{19}$ and $R_{20}$ being as defined above; or, in the case where m is 2, $R_1$ is $C_2$-$C_{12}$alkanedioxy or $C_3$-$C_{25}$alkanedioxy which is interrupted by oxygen; or, in the case where m is 3, $R_1$ is $C_3$-$C_{10}$alkanetrioxy; or, in the case where m is 4, $R_1$ is

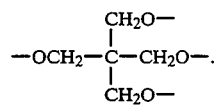

3. A composition according to claim 1, in which at least two of the radicals $R_2$, $R_3$, $R_4$ and $R_5$ are hydrogen.

4. A composition according to claim 3, in which $R_3$ and $R_5$ are hydrogen.

5. A composition according to claim 1, in which m is 1.

6. A composition according to claim 1, in which $R_3$, $R_5$, $R_7$ and $R_{10}$, independently of one another, are hydrogen or $C_1$-$C_4$alkyl, $R_2$ is hydrogen or $C_1$-$C_{18}$alkyl, $R_4$ is hydrogen, $C_1$-$C_{12}$alkyl, $C_1$-$C_8$alkoxy or $-(CH_2)_n-COR_{14}$, in which n is 0, 1 or 2, $R_{14}$ is hydroxyl or $C_1$-$C_{12}$alkoxy, $R_{11}$ and $R_{12}$, independently of one another, are hydrogen or $C_1$-$C_4$alkyl, m is 1 and $R_1$ is hydroxyl, $C_1$-$C_{18}$alkoxy, $C_3$-$C_{18}$alkoxy which is interrupted by oxygen; unsubstituted or $C_1$-$C_8$alkyl-substituted phenoxy

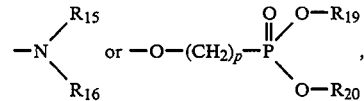

$R_{15}$ and $R_{16}$, independently of one another, being hydrogen or $C_1$-$C_{12}$alkyl.

7. A composition according to claim 1, in which m is 1, $R_1$ is hydroxyl, $C_1$-$C_{18}$alkoxy, $C_3$-$C_{18}$alkoxy which is interrupted by oxygen, unsubstituted or $C_1$-$C_8$alkyl-substituted phenoxy;

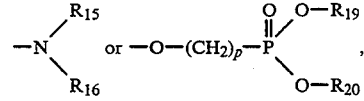

$R_{15}$ and $R_{16}$, independently of one another, being hydrogen or $C_1$-$C_{12}$alkyl, $R_2$ is hydrogen, $C_1$-$C_{18}$alkyl or cyclohexyl, $R_3$, $R_5$, $R_7$ and $R_{10}$ are hydrogen, or the radicals $R_2$ and $R_3$ together with the carbon atoms to which they are bonded form a phenyl ring, $R_4$ is hydrogen, $C_1$-$C_6$alkyl, cyclohexyl, $C_1$-$C_4$alkoxy or $-(CH_2)_2-COR_{14}$, in which $R_{14}$ is $C_1$-$C_4$alkyl, $R_8$, $R_9$, $R_{11}$ and $R_{12}$, independently of one another, are hydrogen or $C_1$-$C_4$alkyl, and, in the case where $R_6$ is hydrogen, $R_4$ is additionally a radical of the formula (2),

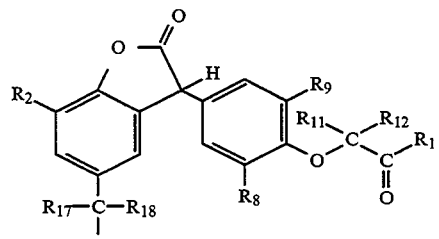

(2)

in which $R_1$, $R_2$, $R_8$, $R_9$, $R_{11}$ and $R_{12}$ are as defined above, $R_{17}$ and $R_{18}$, independently of one another, are hydrogen or $C_1$-$C_4$alkyl, or $R_{17}$ and $R_{18}$ together with the carbon atom to which they are bonded form a $C_5$–$C_7$cycloalkylidene ring, $R_6$ is hydrogen or a radical of the formula (3),

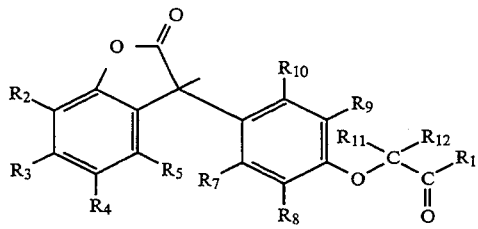
(3)

in which $R_1$, $R_2$, $R_3$, $R_4$, $R_5$, $R_7$, $R_8$, $R_9$, $R_{10}$, $R_{11}$ and $R_{12}$ are as defined above.

8. A composition according to claim 1, in which m is 1, $R_1$ is hydroxyl, $C_1$–$C_{18}$alkoxy, unsubstituted or $C_1$–$C_4$alkyl-substituted phenoxy;

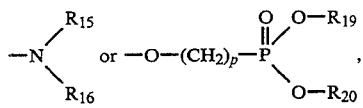

$R_{15}$ and $R_{16}$, independently of one another, being hydrogen or $C_1$–$C_4$alkyl, p being 1 or 2, and $R_{19}$ and $R_{20}$ being $C_1$–$C_4$alkyl, $R_2$ is hydrogen or $C_1$–$C_{18}$alkyl, $R_3$, $R_5$, $R_7$, $R_{10}$, $R_{11}$ and $R_{12}$ are hydrogen, $R_4$ is hydrogen or $C_1$–$C_4$alkyl, and, in the case where $R_6$ is hydrogen, $R_4$ is additionally a radical of the formula (2),

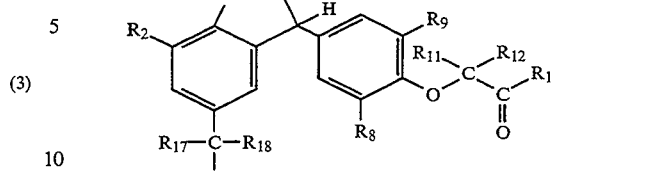
(2)

$R_{17}$ and $R_{18}$ together with the carbon atom to which they are bonded form a cyclohexylidene ring, $R_8$ and $R_9$, independently of one another, are hydrogen or $C_1$–$C_4$alkyl, $R_6$ is hydrogen or a radical of the formula (3),

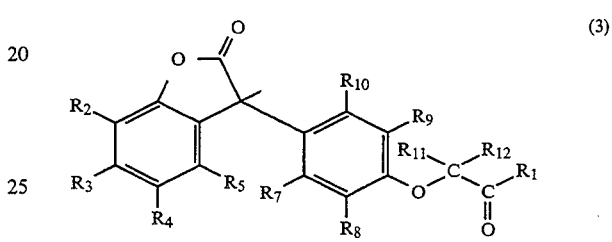
(3)

in which $R_1$, $R_2$, $R_3$, $R_4$, $R_5$, $R_7$, $R_8$, $R_9$, $R_{10}$, $R_{11}$ and $R_{12}$ are as defined above.

9. A composition according to claim 1, in which component a) is a synthetic polymer.

10. A composition according to claim 1, in which component b) is present in an amount of 0.0005 to 5%, relative to the weight of component a).

11. A composition according to claim 1 additionally containing an organic phosphite or phosphonite.

12. A process for the stabilisation of an organic material against oxidative, thermal or light-induced degradation which comprises incorporating therein or applying thereto at least one compound of the formula (1) defined in claim 1.

* * * * *